(12) United States Patent
Mueller et al.

(10) Patent No.: US 10,481,376 B2
(45) Date of Patent: Nov. 19, 2019

(54) SURGICAL MICROSCOPE HAVING OPTICAL INTERFACES

(71) Applicant: Carl Zeiss Meditec AG, Jena (DE)

(72) Inventors: Andre Mueller, Koenigsbronn-Zang (DE); Daniel Kolster, Oberkochen (DE); Christian Luecke, Oberkochen (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 381 days.

(21) Appl. No.: 15/050,311

(22) Filed: Feb. 22, 2016

(65) Prior Publication Data

US 2016/0170194 A1 Jun. 16, 2016

Related U.S. Application Data

(63) Continuation of application No. PCT/EP2014/067491, filed on Aug. 15, 2014.

(30) Foreign Application Priority Data

Aug. 20, 2013 (DE) ........................ 10 2013 216 476

(51) Int. Cl.
*G02B 21/22* (2006.01)
*G02B 21/00* (2006.01)

(52) U.S. Cl.
CPC ......... *G02B 21/22* (2013.01); *G02B 21/0012* (2013.01)

(58) Field of Classification Search
CPC ........ G02B 5/04; G02B 17/04; G02B 17/045; G02B 21/00; G02B 21/0004;

(Continued)

(56) References Cited

U.S. PATENT DOCUMENTS 3,173,984 A 3/1965 Vogl
3,574,295 A 4/1971 Tasaki
(Continued)

FOREIGN PATENT DOCUMENTS

DE 33 18 011 A1 11/1984
DE 299 23 951 U1 10/2001
(Continued)

OTHER PUBLICATIONS

International Preliminary Report on Patentability and Written Opinion dated Mar. 3, 2016 of international application PCT/EP2014/067491 on which this application is based.
(Continued)

*Primary Examiner* — Thomas K Pham
*Assistant Examiner* — Ibrahima Diedhiou
(74) *Attorney, Agent, or Firm* — Walter Ottesen, P.A.

(57) ABSTRACT

An input coupling module selectively couples a beam path into a first or second stereoscopic component beam in a surgical microscope having an optical interface for guiding a beam path to be coupled-in. The input coupling module has a first beam splitter arranged in the first component beam and a second beam splitter arranged in the second component beam. The input coupling module contains an adjustable optics assembly, which selectively guides a beam path provided at the optical interface for coupling into the first or second component beam to the first beam splitter or the second beam splitter. The adjustable optics assembly includes an optical element displaceable by a linear movement from a first position to a second, position, and vice versa, for switching the beam path. The displaceable optical element is arranged in the beam path to be coupled-in in the first position and/or the second position.

17 Claims, 18 Drawing Sheets

(58) Field of Classification Search
CPC ............ G02B 21/0012; G02B 21/0088; G02B 21/02; G02B 21/025; G02B 21/18; G02B 21/20; G02B 21/22; G02B 21/26; G02B 21/361; G02B 21/365; G02B 27/144; G02B 27/2264; G02B 27/286; G03B 17/48; G03B 35/00; G03B 35/10; A61B 1/00188; A61B 1/00193; A61B 1/00195; A61B 3/13; A61B 3/132; A61B 90/00; A61B 90/20; A61B 90/36; A61B 90/50; G01N 21/8851
USPC ....... 359/362, 363, 368, 372–380, 381, 383, 359/384, 385, 388, 389, 407, 431, 432, 359/462, 629, 638, 696, 831, 833; 351/205, 216, 220; 355/22; 396/326, 396/432, 324; 600/166, 168, 476; D16/131; 348/42, 49, 79
See application file for complete search history.

(56) References Cited

U.S. PATENT DOCUMENTS

| | | | |
|---|---|---|---|
| 4,685,776 A | 8/1987 | Inoue et al. | |
| 5,009,487 A | 4/1991 | Reiner | |
| 5,126,877 A | 6/1992 | Biber | |
| 5,579,772 A | 12/1996 | Kinukawa et al. | |
| 5,867,309 A | 2/1999 | Spink et al. | |
| 6,081,371 A | 6/2000 | Shioda et al. | |
| 6,088,155 A | 7/2000 | Tandler et al. | |
| 6,598,972 B2 | 7/2003 | Strahle | |
| 6,661,572 B2 | 12/2003 | Spink et al. | |
| 6,804,051 B2 | 10/2004 | Deverin | |
| 7,002,738 B2 | 2/2006 | Sturgis et al. | |
| 7,894,130 B2 | 2/2011 | Knuenz et al. | |
| 2001/0010592 A1 | 8/2001 | Nakamura | |
| 2008/0100893 A1* | 5/2008 | Knuenz ................. | G02B 21/22 359/196.1 |
| 2013/0229626 A1 | 9/2013 | Zuend et al. | |

FOREIGN PATENT DOCUMENTS

EP    1 666 948 A2   6/2006
JP    10-133122 A    5/1998

OTHER PUBLICATIONS

International Search Report dated Apr. 2, 2015 of international application PCT/EP20141067491 on which this application is based.
English translation and German Office action dated Dec. 17, 2013 of German application 10 2013 216 476.9 on which the claim of priority is based.

* cited by examiner

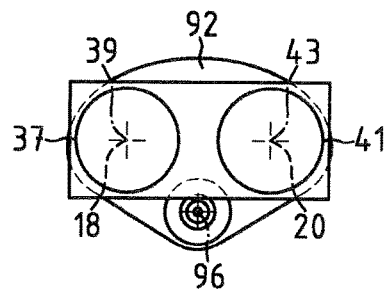 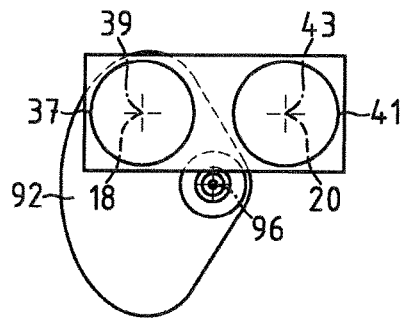
Fig.12　　　　　　　　Fig.13
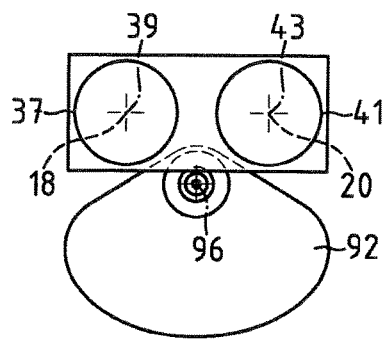 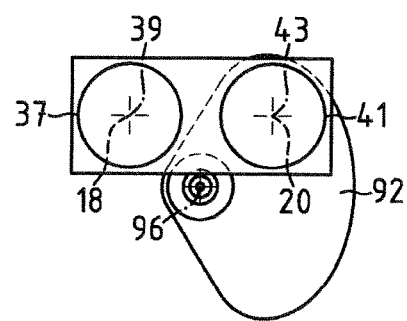
Fig.14　　　　　　　　Fig.15

SURGICAL MICROSCOPE HAVING OPTICAL INTERFACES

CROSS REFERENCE TO RELATED APPLICATIONS

This application is a continuation application of international patent application PCT/EP2014/067491, filed Aug. 15, 2014, designating the United States and claiming priority from German application 10 2013 216 476.9, filed Aug. 20, 2013, and the entire content of both applications is incorporated herein by reference.

FIELD OF THE INVENTION

The invention relates to a surgical or operating microscope for the stereoscopic observation of an operation region, with a first stereoscopic partial beam path and comprising a second stereoscopic partial beam path and with an input coupling module for selectively coupling a beam path provided at an optical interface into the first or second stereoscopic partial beam path. Moreover, the invention relates to an operating microscope with an output coupling module for selectively decoupling a beam path from the first or the second stereoscopic partial beam path in the operating microscope to an optical interface.

Moreover, the invention relates to an input and output coupling module for selectively coupling or decoupling a beam path in an optical instrument, more particularly an operating microscope, and an operating microscope with such an input and output coupling module.

BACKGROUND OF THE INVENTION

An input and output coupling module of the type set forth at the outset is known from U.S. Pat. No. 6,804,051 B1. Using this, a beam path in the case of an operating microscope can be selectively coupled from a first optical interface into a first or second stereoscopic partial beam path of the operating microscope and it is additionally possible to decouple a further beam path to a further optical interface from the first or the second stereoscopic partial beam path. To this end, the input and output coupling module contains a first beam splitter arranged in the first stereoscopic partial beam path and a second beam splitter arranged in the second stereoscopic partial beam path. There is a first adjustable optics assembly in the input and output coupling module, the adjustable optics assembly guiding the beam path from the first optical interface selectively to the first beam splitter or the second beam splitter. The input and output coupling module moreover contains a further adjustable optics assembly for guiding the beam path decoupled from the first or second stereoscopic partial beam path of the operating microscope to the further optical interface. The adjustable optics assemblies in the input and output coupling module contain, in each case, two prism blocks displaceable by a linear movement from a first position to a second position, and vice versa, relative to the optical interfaces, for switching the beam path provided at the optical interface for coupling-in and the beam path guided to the optical interface for decoupling. These prism blocks each have two mirror surfaces. Of these prism blocks, respectively one is positioned in the beam path to be coupled-in and another one is positioned in the beam path to be decoupled.

EP 1 666 948 A2 describes an operating microscope with an input coupling module. In this operating microscope, a rotatable mirror is arranged between the first (left-hand) and second (right-hand) stereoscopic partial beam path for the stereoscopic observation of an object region through a main objective of the microscope. Using this rotatable mirror, the image information supplied from an optical interface can selectively be guided from a display to a beam splitter arranged in the left and right observation beam path. In accordance with the position of the rotatable mirror, the image information depicted at the display is then coupled either into the left-hand or into the right-hand observation beam path and thus superposed on the observation image of the object region.

U.S. Pat. No. 7,002,738 describes an operating microscope with an output coupling module having an optical interface, at which the light from a left-hand and right-hand stereoscopic partial beam path can selectively be provided for the object observation. To this end, there are beam splitters mounted in a rotationally movable manner in the first and the second stereoscopic partial beam path of the operating microscope, the beam splitters guiding the observation light to a switchable mirror element which directs it to an optical interface.

SUMMARY OF THE INVENTION

Proceeding herefrom, it is an object of the invention to provide a switchable input and/or output coupling module with a compact configuration, by means of which a beam path guided to a stationary optical interface in an optical instrument, for example, a surgical microscope, can be selectively coupled into a first or second stereoscopic partial beam path and/or by means of which a beam path selectively decoupled from the first or second stereoscopic partial beam path can be made available at a stationary optical interface.

Surgical microscopes are often used by groups of surgeons, some of whom have a right guiding eye and others have a left guiding eye. Depending on whether the guiding eye is on the left or right, monocular mirroring of data into either the left-hand or right-hand stereoscopic partial observation beam path is desirable for the surgeons.

If there is a demand for the image data mirrored into an operating microscope to have a reference to the observation, for example if images are displayed to the surgeon in a manner superposed onto the operation region visible in the operating microscope, the location, size and orientation of the images being adapted to the image of the operating region perceived by the observer, for example for the purposes of displaying the orientation of the patient eye in ophthalmic surgery (eye tracking), it is advantageous, for the purposes of avoiding parallax errors, in an operating microscope for there to be both decoupling of a beam path from a stereoscopic partial observation beam path to a camera and a device, connected therewith, for image evaluation and also coupling-in of a beam path with location and orientation information in one and the same stereoscopic partial observation beam path in the operating microscope.

Against this backdrop, it is desirable, particularly in the case of ophthalmic operating microscopes, for it to be possible to select the stereoscopic partial beam path, from which a beam path to a camera is decoupled and into which the image of a display is coupled.

Therefore, it is also an idea of the invention to provide an operating microscope for the stereoscopic observation of an operating region, with a first and a second stereoscopic partial beam path, the operating microscope containing an input coupling module for selectively coupling-in a beam path which is guided from a display by an optical interface that is stationary in relation to the operating microscope.

Furthermore, it is an idea of the invention to provide, in such an operating microscope, an output coupling module for selectively decoupling a beam path from a first or second stereoscopic partial beam path to an interface that is stationary in the operating microscope.

An input coupling module according to the invention and an output coupling module according to the invention therefore have an adjustable optics assembly for switching the beam path from a first position to a second position, and vice versa. This adjustable optics assembly contains at least one optical element preferably displaceable by linear movement, the optical element being arranged in the beam path to be coupled-in or to be decoupled, respectively, in the first position and/or the second position.

Here, the invention is based on the concept that a very compact configuration is made possible for the input coupling module if different optical path lengths are accepted for coupling a beam path, which has been guided to an optical interface, into the two stereoscopic partial beam paths using an input coupling module having an adjustable optics assembly in the case of an operating microscope. A corresponding statement applies for the selective decoupling of a beam path from the first or second stereoscopic partial beam path in an operating microscope for the purposes of providing the decoupled beam path at an optical interface.

Moreover, it is an idea of the invention to minimize the number of movable assemblies in such an input or output coupling module in order to keep production costs low in this way.

By way of example, this at least one optical element can be a mirror element which deflects the beam path to be coupled-in in the first position and/or the second position.

Preferably, the adjustable optics assembly also contains at least a further mirror element, wherein the displaceable mirror element is arranged in the beam path to be coupled-in in the first position and directs the beam path to the further mirror element guiding the beam path to the first beam splitter for the coupling into the first stereoscopic partial beam path and enabling the beam path to be coupled-in in the second position such that the beam path reaches the second beam splitter for the purposes of coupling into the second stereoscopic partial beam path.

In an input or output coupling module according to the invention, there advantageously is a support frame receiving the optics assembly, in which support frame the further mirror element is held at an adjustment device, by means of which the mirror element can be adjusted for setting the optical axis of the beam path guided to the first beam splitter. To this end, the adjustment device is preferably, for example, embodied in such a way that the mirror element can be displaced about a first movement axis and about a second movement axis that differs from the first movement axis.

According to the invention, the input coupling module has an interface with an optical axis. In the present case, the optical axis of an interface should be understood to mean the axis of symmetry of the beam path which passes through the interface. In the input coupling module there is a first observation channel passing through the first beam splitter and having an optical axis, and a second observation channel passing through the second beam splitter, the second observation channel likewise having an optical axis. In the present case, the optical axis of an observation channel is understood to mean the axis of symmetry of the optical beam path guided in the observation channel. The optical axis of the first observation channel and the optical axis of the second observation channel in the input coupling module in this case lie in a common plane perpendicular to the optical axis of the interface. The optical axis of the interface then passes through the first or the second beam splitter. Here, in particular, the optical axis of the interface can intersect the optical axis of the first or the second observation channel.

However, the input coupling module can also have a first observation channel passing through the first beam splitter and having an optical axis, and a second observation channel passing through the second beam splitter and having an optical axis, with the optical axis of the first observation channel and the optical axis of the second observation channel lying in a common plane parallel to the optical axis of the interface.

In particular, an idea of the invention is to provide a support frame receiving the optics assembly in the input coupling module, in which support frame the mirror element displaceable by linear movement is held at an adjustment device, by means of which the mirror element can be adjusted for setting the optical axis of the beam path guided to the first beam splitter and to the second beam splitter.

Moreover, it is an idea of the invention that the adjustable optics assembly contains a shutter element displaceable by linear movement, for selectively covering the first beam splitter or the second beam splitter. In particular, the shutter element can be embodied as a perforated diaphragm through which a beam path which has been guided to the optical interface passes.

The adjustable optics assembly can also contain a further mirror element displaceable by linear movement and coupled in terms of movement to the mirror element, with the mirror element and the further mirror element being able to be moved from a first position to a second position, and vice versa. Here, the mirror element and the further mirror element are arranged in the beam path to be coupled-in in the first position and they direct the beam path to the first beam splitter. They enable the beam path to be coupled-in in the second position so that the latter reaches the second beam splitter for coupling into the second stereoscopic partial beam path.

In this case, the input coupling module can likewise have a support frame receiving the optics assembly, the support frame holding the mirror element and/or the further mirror element at an adjustment device, by means of which the mirror element and/or the further mirror element can be adjusted for setting the optical axis of the beam path guided to the first beam splitter. To this end, the adjustment device renders it possible, for example, that the mirror element can be displaced about a first movement axis and about a second movement axis that differs from the first movement axis.

It is advantageous if the adjustable optics assembly contains a shutter element displaceable by linear movement and coupled in terms of movement with the first mirror element and the further mirror element, the shutter element covering the second beam splitter in the first position of the mirror element and the further mirror element and covering the first beam splitter in the second position of the first mirror element and the further mirror element.

It is also possible to embody the shutter element displaceable by linear movement as a perforated diaphragm with an aperture, through which a beam path which can be guided to the optical interface passes.

The optical element can be embodied as a shutter element, in particular in the form of a perforated diaphragm with an aperture, displaceable by linear movement, through which the beam path passes in the first position and in the second position, wherein the adjustable optics assembly contains a third beam splitter which splits the beam path to be coupled-in, which can be guided to the optical interface, into a first partial beam path and into a second partial beam path, wherein the first partial beam path is guided to the second beam splitter and the second partial beam path is guided to a mirror element deflecting the second partial beam path to the first beam splitter, wherein the perforated diaphragm covers the first beam splitter in the first position and the aperture uncovers the second beam splitter for the first partial beam path and the perforated diaphragm covers the second beam splitter in the second position and the aperture uncovers the first beam splitter for the second partial beam path.

According to the invention, this optics assembly has an interface with an optical axis and contains a first observation channel, which passes through the first beam splitter and has an optical axis, and a second observation channel, which passes through the second beam splitter and has an optical axis. The optical axis of the first observation channel and the optical axis of the second observation channel in this case lie in a common plane parallel or perpendicular to the optical axis of the interface. If the optical axis of the interface is perpendicular to the plane spanned by the optical axes of the first and the second observation channel, the optical axis of the interface preferably passes through the optical axis of the first or the second beam splitter. Here, the optical axis of the interface then intersects the optical axis of the first or the second observation channel.

It is advantageous if the input coupling module has a support frame receiving the optics assembly, in which support frame the mirror element is held at an adjustment device, by means of which the mirror element can be adjusted for setting the optical axis of the beam path guided to the first beam splitter.

An output coupling module according to the invention also preferably has a further mirror element in the adjustable optics assembly in addition to the mirror element displaceable by linear movement from a first position to a second position that deflects the decoupled beam path in the first and/or the second position. Here, the further mirror element guides a stereoscopic partial beam path decoupled by the first beam splitter to the further mirror element, wherein the mirror element displaceable by linear movement, in the first position, receives the partial beam path decoupled by the first beam splitter from the further mirror element and guides the beam path to the optical interface and, in the second position, enables the partial beam path decoupled by the second beam splitter for passing through to the optical interface.

The output coupling module can also have a support frame receiving the optics assembly, in which support frame the further mirror element are/is held at an adjustment device, by means of which the mirror element can be adjusted for setting the optical axis of the beam path guided from the first beam splitter.

The output coupling module has an interface with an optical axis, to which a camera can be connected. A first observation channel, which passes through the first beam splitter and has an optical axis, and a second observation channel, which passes through the second beam splitter and has an optical axis, are guided through the output coupling module. The optical axis of the first observation channel and the optical axis of the second observation channel in this case lie in a common plane perpendicular to the optical axis of the interface.

In the present case, the optical axis of an observation channel is also understood to mean the axis of symmetry of the optical beam path guided in the observation channel. In the present case, the optical axis of an interface should be likewise understood to mean the axis of symmetry of the beam path which passes through the interface.

As an alternative hereto, it is also possible for the optical axis of the first observation channel and the optical axis of the second observation channel to lie in a common plane parallel to the optical axis of the interface.

According to the invention, the output coupling module also has a support frame receiving the optics assembly, in which support frame the mirror element and/or the further mirror element are/is held at an adjustment device, by means of which the mirror element and/or the further mirror element can be adjusted for setting the optical axis of the beam path guided to the first beam splitter, for example by virtue of the mirror element being displaced about a first movement axis and about a second movement axis that differs from the first movement axis.

It is advantageous if this output coupling module has a support frame receiving the optics assembly, in which support frame the first mirror element displaceable by linear movement is also held at an adjustment device, by means of which the mirror element can be adjusted for setting the optical axis of the beam path guided to the first beam splitter and the second beam splitter.

In particular, the adjustable optics assembly can contain a shutter element displaceable by linear movement and coupled in terms of movement with the mirror element displaceable by linear movement, for selectively covering the first or the second beam splitter. Here it is possible, in particular, for this shutter element to be embodied as a perforated diaphragm through which a beam path which has been guided to the optical interface passes.

The adjustable optics assembly can also contain a further mirror element displaceable by linear movement and coupled in terms of movement to the mirror element, wherein the mirror element and the further mirror element can be moved from a first position to a second position, and vice versa, wherein the mirror element and the further mirror element, in the first position, are arranged in the beam path to be decoupled and direct the beam path from the first beam splitter to the optical interface, and wherein the mirror element and the further mirror element, in the second position, enable the beam path to be decoupled, so that the latter reaches the optical interface from the second beam splitter.

According to the invention, the adjustable optics assembly in this case contains a shutter element displaceable by linear movement and coupled in terms of movement with the first mirror element and the further mirror element, the shutter element covering the second beam splitter in the first position of the mirror element and the further mirror element and covering the first beam splitter in the second position of the first mirror element and the further mirror element.

The displaceable optical element is embodied as a shutter element, in particular as a shutter element in the form of a perforated diaphragm with a hole-shaped aperture, wherein the adjustable optics assembly contains a mirror element which directs a beam path decoupled from the first stereoscopic partial beam path by means of the first beam splitter to a further beam splitter guiding the beam path to the optical interface, wherein the further beam splitter guides a beam path decoupled by means of the second beam splitter from the second stereoscopic partial beam path to the optical interface, and wherein the shutter element, in the first position, blocks the beam path decoupled by means of the first beam splitter and enables the beam path decoupled by means of the second beam splitter and, in the second position, enables the beam path decoupled by means of the first beam splitter and blocks the beam path decoupled by means of the second beam splitter.

The output coupling module may have a first observation channel, which passes through the first beam splitter and has an optical axis, and a second observation channel, which passes through the second beam splitter and has an optical axis, wherein the optical axes of the first and the second observation channel lie in a common plane, and wherein the optical interface, for the provision of the beam path, has an optical axis parallel to the common plane or an optical axis perpendicular to the common plane. If the optical axis of the interface is perpendicular to the plane spanned by the optical axes of the first and the second observation channel, the optical axis of the interface preferably passes through the optical axis of the first or the second beam splitter. Here, the optical axis of the interface then intersects the optical axis of the first or the second observation channel.

Here, it is also advantageous if the output coupling module contains a support frame receiving the optics assembly, in which support frame the mirror element is held at an adjustment device, by means of which the mirror element can be adjusted for setting the optical axis of the beam path guided by the first beam splitter, preferably by displacement about a first movement axis and about a second movement axis that differs from the first movement axis.

The invention also extends to a module for the selective coupling of a beam path into a first or second stereoscopic partial beam path in an operating microscope and the selective decoupling of a beam path from a first or second stereoscopic partial beam path in an operating microscope. This module can have an adjustable shutter for selectively enabling and interrupting the first stereoscopic partial beam path and/or the second stereoscopic partial beam path between the input coupling module and the output coupling module.

An input or output coupling module according to the invention can be substantially constructed from plane optical units. Therefore, it can be produced in compact configurations in a cost-effective manner with little adjustment outlay. As a result of the compact configuration, such an input or output coupling module is suited, in particular, for use in various operating microscopes. An idea of the invention therefore also consists of configuring an input or output coupling module as a modular assembly or platform assembly, which is suitable for use in various operating microscope types.

By way of example, in the case of an operating microscope which only contains one display for mirroring-in data and merely one camera for acquiring images of the object region, the invention thus renders it possible to selectively guide a beam path decoupled from the first or second stereoscopic partial beam path to the camera and couple the image information shown by means of the display into the first or second stereoscopic partial beam path.

Using an input or output coupling module according to the invention, simple electromotive switching between a first and a second stereoscopic partial beam path is also possible. Using this, it is possible, for example in an operating microscope during ongoing surgical operation, for the display information of a single display to be selectively coupled into the first or the second stereoscopic partial beam path and it is possible to decouple the image of the object region either from the first or the second stereoscopic partial beam path, in order to guide it to a camera.

The invention also extends to a surgical microscope for the stereoscopic observation of an operating region, with a first stereoscopic partial beam path and with a second stereoscopic partial beam path, the surgical microscope containing a switchable system for interchanging the beam and image erection for the selective interchange of the first and second stereoscopic partial beam path and for setting an image erection for the image of an object region provided for an observer at a left and a right eyepiece. The operating microscope likewise contains an input and output coupling module for selectively coupling a beam path from a display into the first or second stereoscopic partial beam path and for selectively decoupling a beam path from the first or second stereoscopic partial beam path to a camera. The system for interchanging the beam and image erection in this case is connected to the input and output coupling module by way of a coupling device which, when the system for interchanging the beam and image erection is switched over, switches over the input coupling module and/or the output coupling module in order to couple the beam path from the display into a different one of the two stereoscopic partial beam paths and in order to guide another one of the two stereoscopic partial beam paths to the camera. What is possible to ensure in this case is that, for an observer at the surgical microscope, image information is decoupled from that observation beam path and coupled into that observation beam path which is guided to a specific eye of the observer prior to switching over the system for interchanging the beam and image erection. In particular, this renders it possible to ensure that the guide eye of the observer always obtains the display information mirrored into a specific stereoscopic partial beam path upstream of the system for interchanging the beam and image erection, independently of the switching state of this system.

BRIEF DESCRIPTION OF THE DRAWINGS

The invention will now be described with reference to the drawings wherein:

FIGS. 12 to 15 show a partial view of the further module assembly with different shutter settings;

DESCRIPTION OF THE PREFERRED EMBODIMENTS OF THE INVENTION

Figure 1:
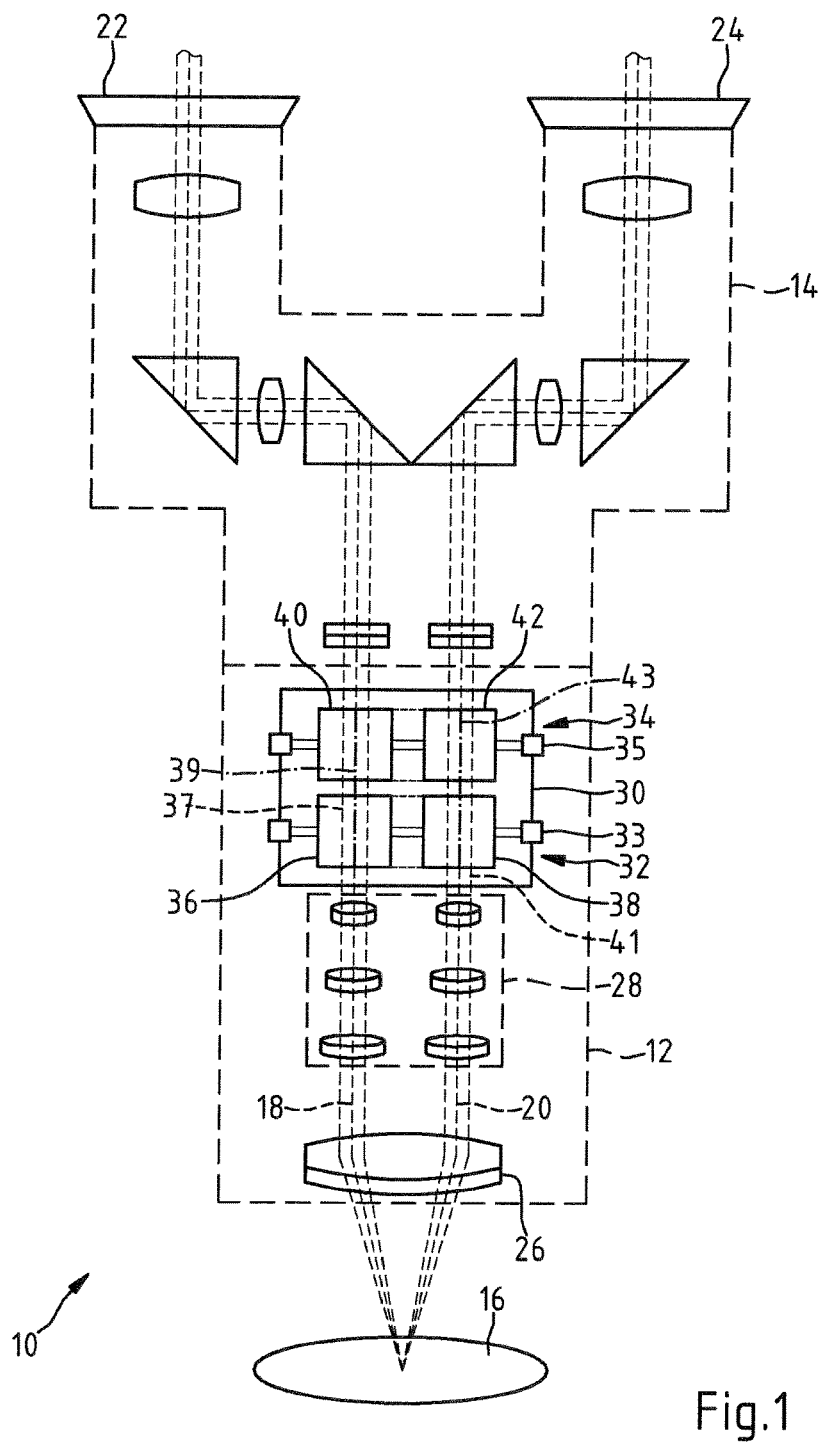
FIG. 1 shows a surgical microscope for the stereoscopic observation of an object region, with a magnification system and a module assembly embodied as an input and output coupling module.

The surgical microscope 10 shown in FIG. 1 is held on a carrier apparatus (not shown in any more detail) and it has a main body 12 and a binocular tube 14. The surgical microscope 10 is an optical instrument and allows an observer to observe, in a magnified manner, an object region 16 at a left and right eyepiece (22, 24) by way of a first stereoscopic partial beam path 18 and a second stereoscopic partial beam path 20.

The stereoscopic partial beam paths (18, 20) of the operating microscope 10 pass through a main objective 26 of the microscope held in the main body 12 and they are guided with a parallel imaging beam path through a magnification system 28 held in the main body 12. The magnification system 28 has a zoom system. A module assembly 30 is arranged in the main body 12 at the end of the magnification system 28 facing away from the main objective 26 of the microscope. The module assembly 30 is situated in the parallel imaging beam path of the surgical microscope 10. The module assembly 30 is an input and output coupling module. The module assembly 30 contains an input coupling module 34 for selectively coupling a beam path which has been guided to a first optical interface (not shown here) into the first or the second stereoscopic partial beam path 18, 20. Furthermore, the module assembly 30 contains an output coupling module 32 for selectively decoupling a beam path from the first or second stereoscopic partial beam path 18, 20 to a second optical interface (not shown here) that differs from the first optical interface.

The input coupling module 34 has an adjustable optics assembly arranged at a support frame 33. The coupling module 34 contains a first beam splitter 36 positioned in the first stereoscopic partial beam path 18 and a second beam splitter 38 positioned in the second stereoscopic partial beam path 20. In the surgical microscope 10, an observation channel 37 passes through the first beam splitter 36. The observation channel defines an optical axis 39 and the first stereoscopic partial beam path 18 is guided therein. An observation channel 41 with an optical axis 43, in which the second stereoscopic partial beam path 20 is guided, extends through the second beam splitter 38 in the surgical microscope 10.

The output coupling module 32 also has an adjustable optics assembly arranged in a support frame 35 and it has a first beam splitter 40 arranged in the first stereoscopic partial beam path 18. The observation channel 37 defining the optical axis 39 is guided through the first beam splitter. The module 32 contains a second beam splitter 42 which is situated in the second stereoscopic partial beam path 20 and through which the observation channel 41 with the optical axis 43 extends.

It should be noted that, firstly, the beam splitters (36, 38) in the output coupling module 32 and, secondly, the beam splitters (40, 42) in the input coupling module 34 are preferably embodied as an integral, connected component in each case. This measure reduces the complexity for binocular adjustment and also reduces the requirements on component tolerances. However, in principle, the beam splitters (36, 38) and (40, 42) can also be embodied as spatially separated splitter cubes in a modified embodiment.

Figure 2:
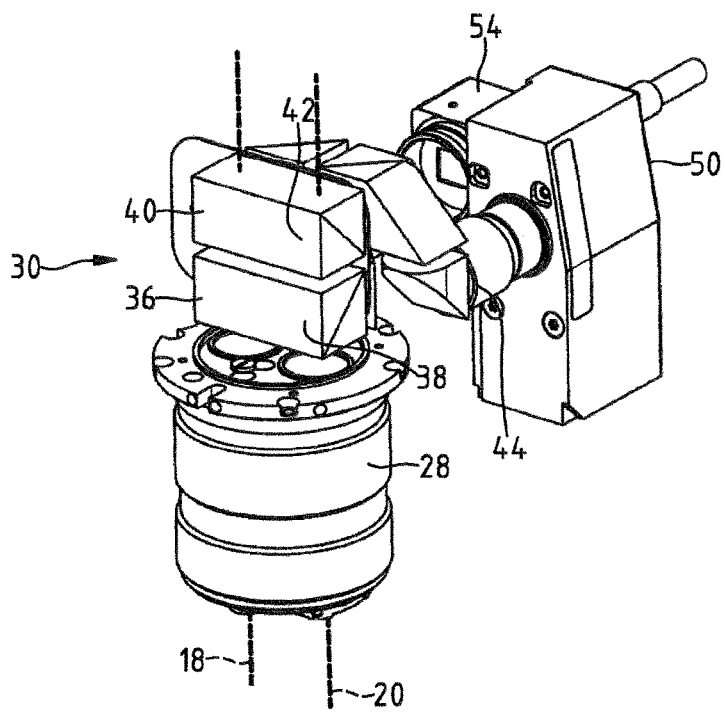
FIG. 2 and FIG. 3 show a perspective view of the module assembly with the magnification system.
Figure 3:
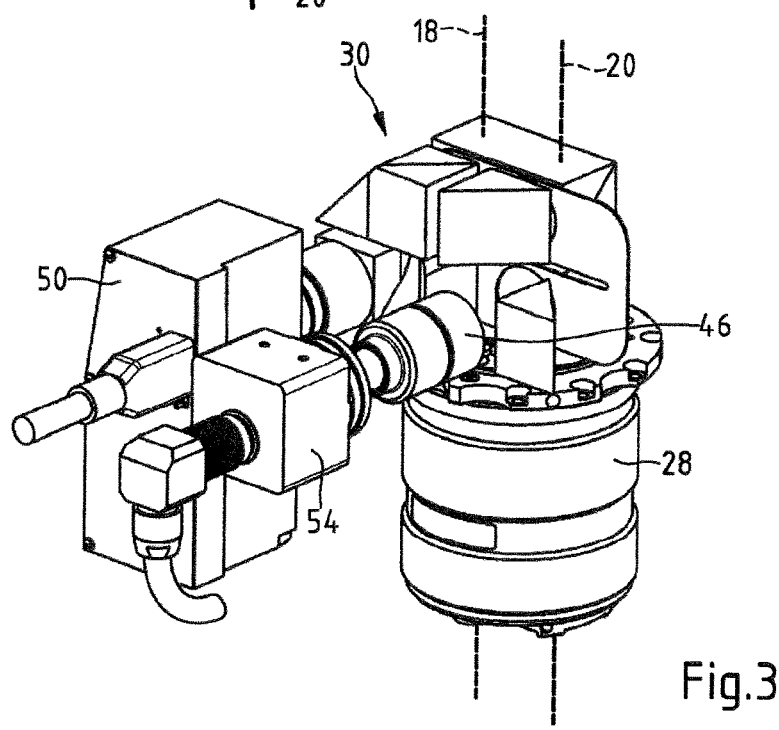

FIG. 2 and FIG. 3 show the module assembly 30 with the first optical interface 44 and the second optical interface 46 and with the magnification system 28 in two different perspective views. Here, the beam splitters (36, 38) on the one hand and the beam splitters (40, 42) on the other hand are configured integrally as a connected prism cube. The display of a display arranged in a display module 50 is guided to the first or second stereoscopic partial beam path (18, 20) in the surgical microscope 10 at the optical interface 44 of the input coupling module 34. As shown in FIG. 2, the display module 50 and the module 30 conjointly define the interface 44 also shown schematically in FIGS. 4 and 5. A beam path to a camera 54, decoupled from the first or second stereoscopic partial beam path (18, 20) in the operating microscope 10, is provided at the optical interface 46 of the output coupling module 32. As shown in FIG. 3, the camera 54 and module 30 conjointly define interface 46 also shown schematically in FIGS. 4 and 5.

Figure 4:
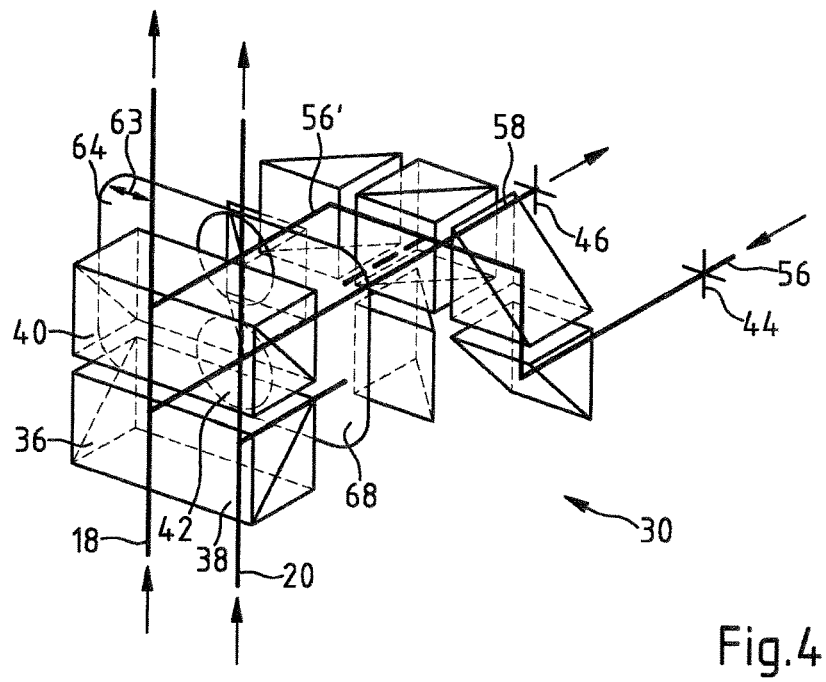
FIG. 4 shows the module assembly in the surgical microscope in a first setting.
Figure 5:
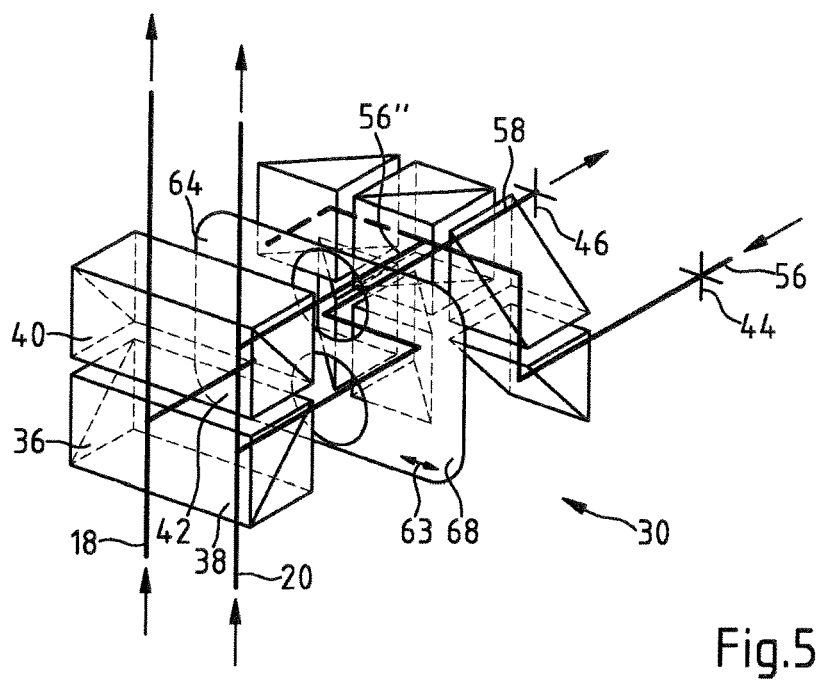
FIG. 5 shows the module assembly in the surgical microscope in a second setting.
Figure 6:
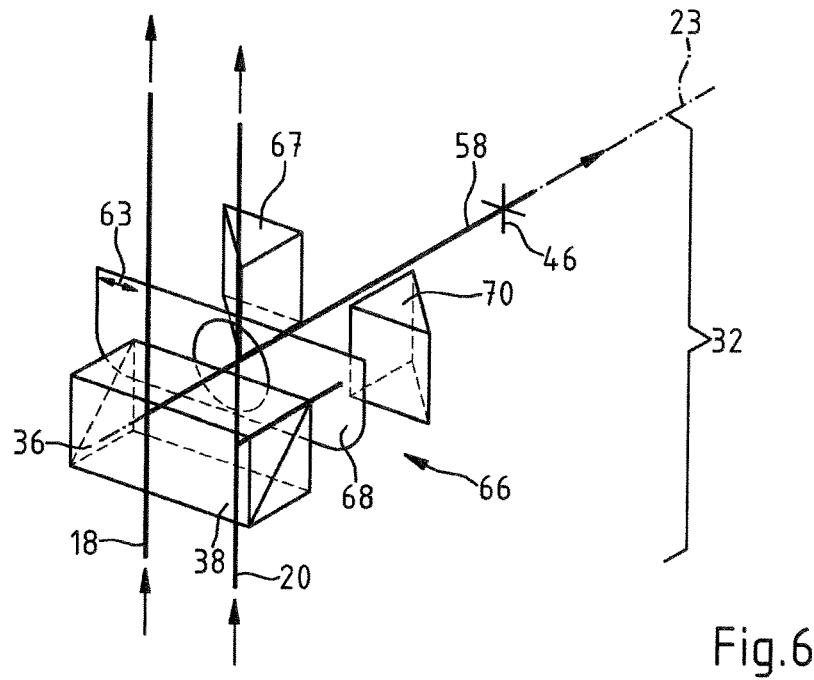
FIG. 6 and FIG. 7 show the output coupling module of the module assembly.
Figure 7:
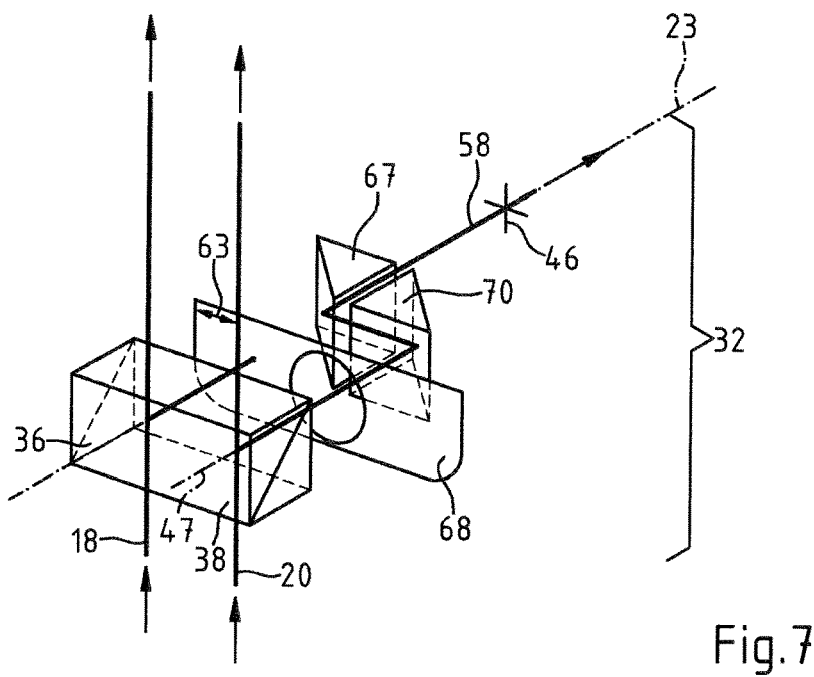
Figure 8:
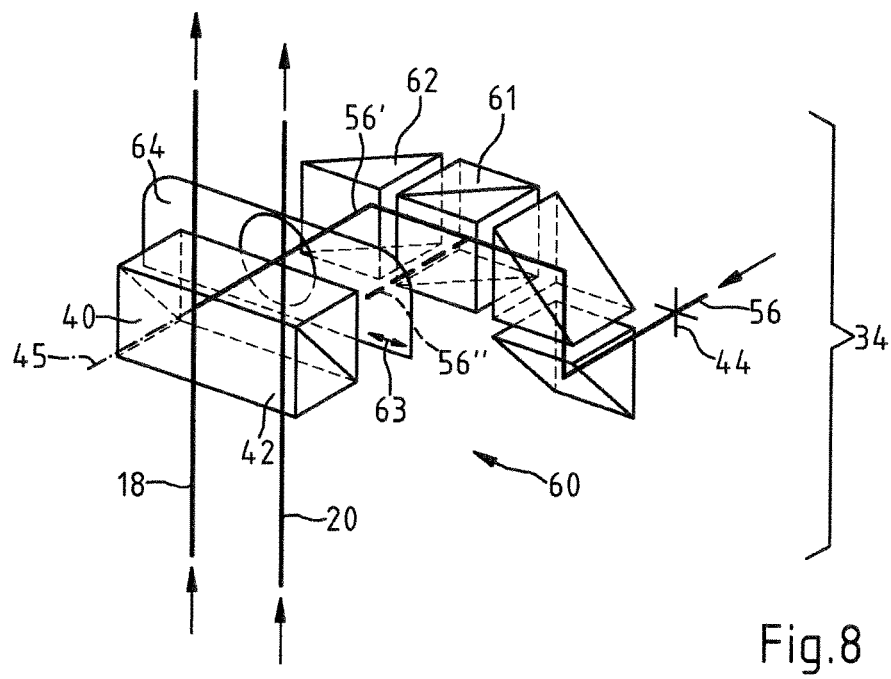
FIG. 8 and FIG. 9 show the input coupling module of the module assembly.
Figure 9:
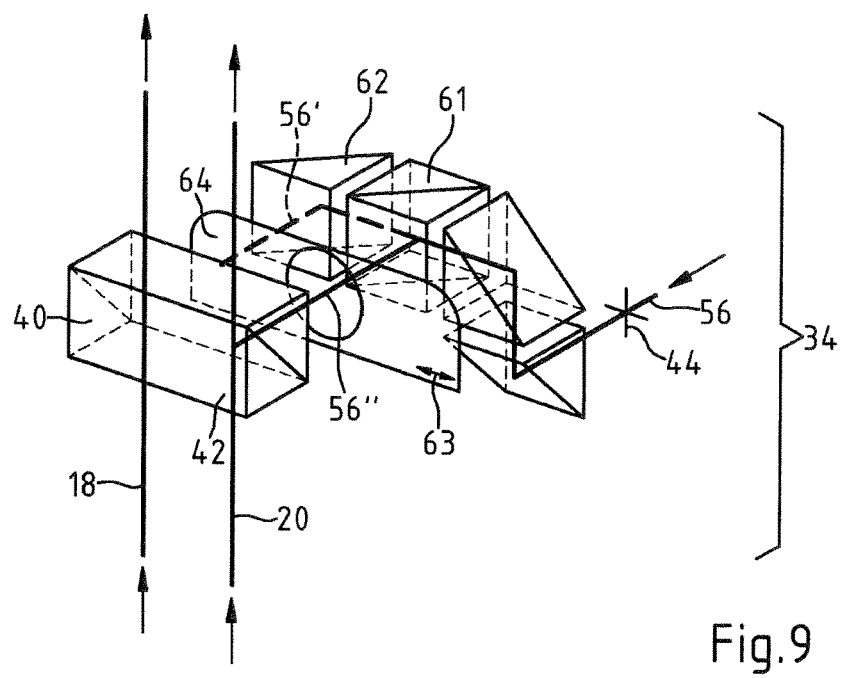

FIG. 4 shows the module assembly 30 with the stereoscopic partial beam paths (18, 20) and a beam path 56, which has been guided to the optical interface 44 and which is coupled into the first stereoscopic partial beam path 18 with the beam path 56', and a beam path 58, which is decoupled from the second stereoscopic partial beam path 20 and provided at the optical interface 46. In FIG. 5, the module assembly 30 is shown in a second setting with a coupled-in beam path 56" and a decoupled beam path 58. FIG. 6 and FIG. 7 show the output coupling module 32 in the module assembly 30 in the first and second setting. In FIG. 8 and FIG. 9, the input coupling module 34 of the module assembly 30 is shown in a first and a second setting.

The output coupling module 32 has an adjustable optics assembly 66 with an optical element displaceable by linear movement which is embodied as a mirror element 67 in the form of a deflection prism, with a further optical element in the form of a perforated diaphragm 68 arranged in a linearly movable manner and acting as a shutter element, and with a further deflection prism, which in turn acts as a mirror element 70. The optical interface 46 of the output coupling module 32 has an optical axis 23, which passes through the beam splitter 36 and intersects the first stereoscopic observation beam path 18.

The input coupling module 34 has an adjustable optics assembly 60, which comprises a beam splitter 61 in the form of a splitter cube and which contains a mirror element 62 embodied as a deflection prism and a perforated diaphragm 64 arranged in a linearly movable manner as a further optical element.

The mirror element 67 is coupled in terms of movement with the perforated diaphragm 68 by way of a coupling mechanism (not shown here). Moreover, the perforated diaphragm 68 which is linearly movable is coupled here in terms of movement with the perforated diaphragm 64. To this end, the perforated diaphragm 68 and the perforated diaphragm 64 are embodied as a connected stop component in the module assembly 30.

A beam path 56 guided to the optical interface 44 is split into a first partial beam path 56' and a second partial beam path 56" by means of the beam splitter 61. The mirror element 62 directs the partial beam path 56' to the beam splitter 40 arranged in the second stereoscopic partial beam path 18. The partial beam path 56' is guided to the first beam splitter 42 arranged in the first stereoscopic partial beam path 20. The perforated diaphragm 64 acts as a shutter element and it can be displaced in the direction of the double-headed arrow 63. As a result of this, it is possible, selectively, to couple the beam path 56 guided to the optical interface 44 into the first stereoscopic partial beam path 18 with the partial beam path 56", with the partial beam path 56" then being interrupted by means of the perforated diaphragm 64, as shown in FIG. 4 and FIG. 8, or, as can be seen in FIG. 5 and FIG. 9, to couple the beam path guided to the optical interface into the second stereoscopic partial beam path 20 with the partial beam path 56", with the first partial beam path 56' then being interrupted by means of the perforated diaphragm 64.

By virtue of the deflection prism 67 and the perforated diaphragm 68 being displaced in the direction of the double-headed arrow 63 in the adjustable optics assembly 66 of the output coupling module 32, it is possible to selectively provide a beam path 58 at the interface 46, the beam path being decoupled from the first stereoscopic partial beam path 18 or the second stereoscopic partial beam path 20 by means of the beam splitter 36 or by means of the beam splitter 38.

Here, the beam path 58 decoupled from the first stereoscopic partial beam path 18 by means of the beam splitter 38 is guided directly to the optical interface 46 in the first setting of the perforated diaphragm 68 and the deflection prism 67. In the second setting of the perforated diaphragm 68 and the deflection prism 67, the beam path decoupled from the second stereoscopic partial beam path 20 by means of the beam splitter 38 is directed from the deflection prism 70 to the deflection prism 67 which thereupon mirrors the decoupled beam path to the optical interface 46.

The deflection prism 67 in the input coupling module 34 and the deflection prism 70 in the output coupling module 32 are held in the support frames (33, 35) of the optical assemblies (60, 66), in each case at an adjustment device allowing the adjustment, about two mutually orthogonal movement axes, of the optical axis (45, 47) of the beam path deflected by means of the mirror element (62, 70).

Figure 10:
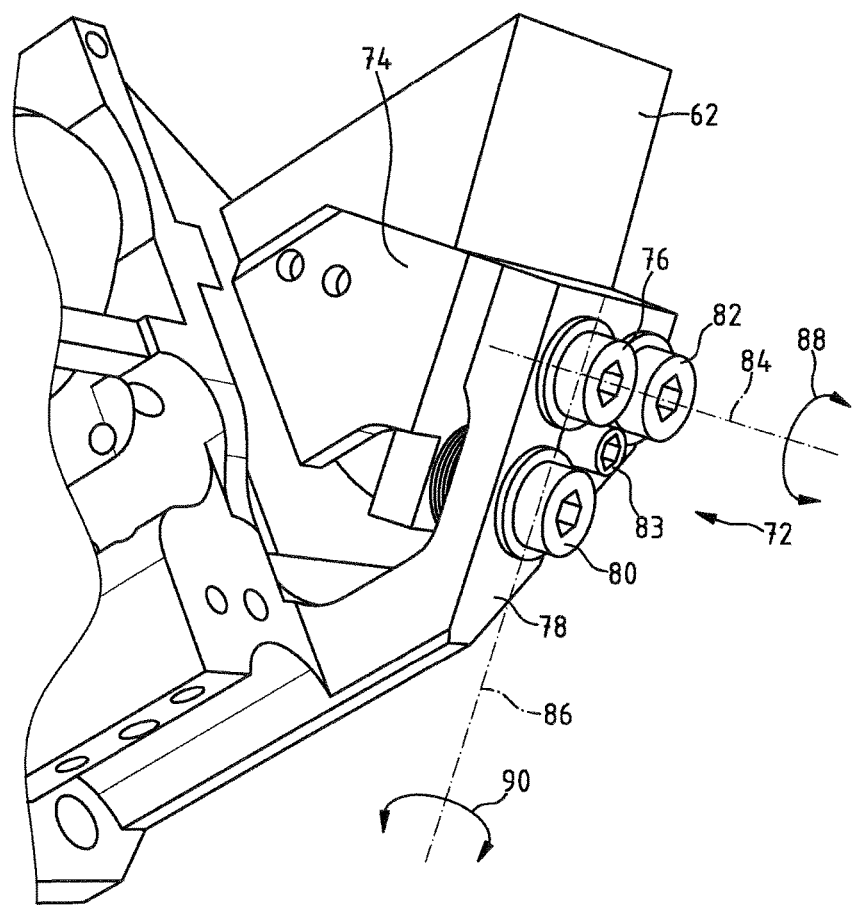
FIG. 10 shows an adjustment device for a mirror element in the module assembly.

FIG. 10 shows the adjustment device 72 for the mirror element 62. The mirror element 62 is secured in a holder 74, which is fastened by way of a fastening screw 76 acting as a pivot screw to a support 78 connected at the support frame 35 of the optics assembly shown in FIG. 1. Adjustment screws (80, 82) are held at the support 78. By adjusting the adjustment screws (80, 82), it is possible to swivel or tilt the holder 74 with the mirror element 62 arranged thereon relative to the support 78 about a first movement axis 84 and about a further movement axis 86 perpendicular to the first movement axis 84 in the directions indicated by means of the double-headed arrows (88, 90). There is a setscrew 83 in the adjustment device 72 for fixing a setting implemented by way of the adjustment screws (80, 82).

Figure 11:
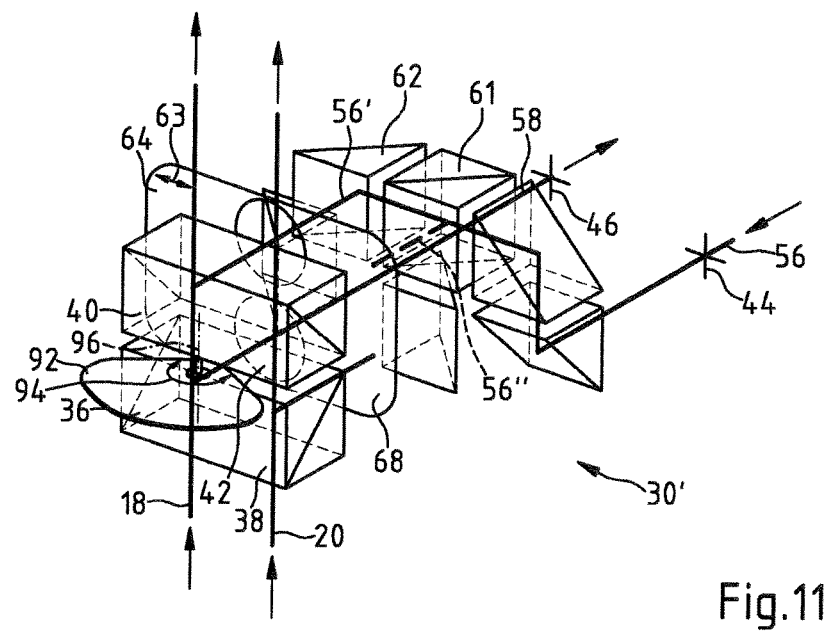
FIG. 11 shows a further module assembly for use in an operating microscope with a shutter.

FIG. 11 shows a module assembly 30', corresponding to the module assembly 30 described above, for use in a stereoscopic operating microscope. To the extent that the optical elements in the module assembly 30' and the optical elements in the module assembly 30 are identical, they have the same reference signs in FIG. 11 as in FIGS. 4 to 9.

The module assembly 30' contains a shutter 92 mounted in a rotationally movable manner, which can be swiveled between the beam splitters (36, 38) of the output coupling module 32 and the beam splitters (40, 42) of the input coupling module 34 in the direction of the double-headed arrow 94 about an axis 96 parallel to the stereoscopic partial beam paths (18, 20) in the operating microscope.

FIGS. 12 to 15 show the shutter 92 with the observation channel 37 having the optical axis 39 for the first stereoscopic partial beam path 18 and the observation channel 41 for the second stereoscopic partial beam path 20 and the optical axis 43 thereof. By swiveling the shutter 92 about the axis 96 it is possible to implement the following settings in the module assembly:

In a first setting, shown in FIG. 12, the first and the second stereoscopic partial beam path (18, 20) are interrupted at the same time. In the setting of FIG. 13, the first partial beam path 18 is interrupted and the second stereoscopic partial beam path 20 is enabled. FIG. 14 shows the shutter in a setting, in which the first and the second stereoscopic partial beam path (18, 20) are simultaneously enabled by the shutter. In the setting of FIG. 15, the first stereoscopic partial beam path 18 is enabled and the second stereoscopic partial beam path 20 is interrupted by means of the shutter 92.

The module assembly 30' enables the display of image information provided at the optical interface 44 in the first and second stereoscopic partial beam path (18, 20) in an operating microscope, selectively superposed on the image of an object region or without an image of the object region being visible.

Figure 16:
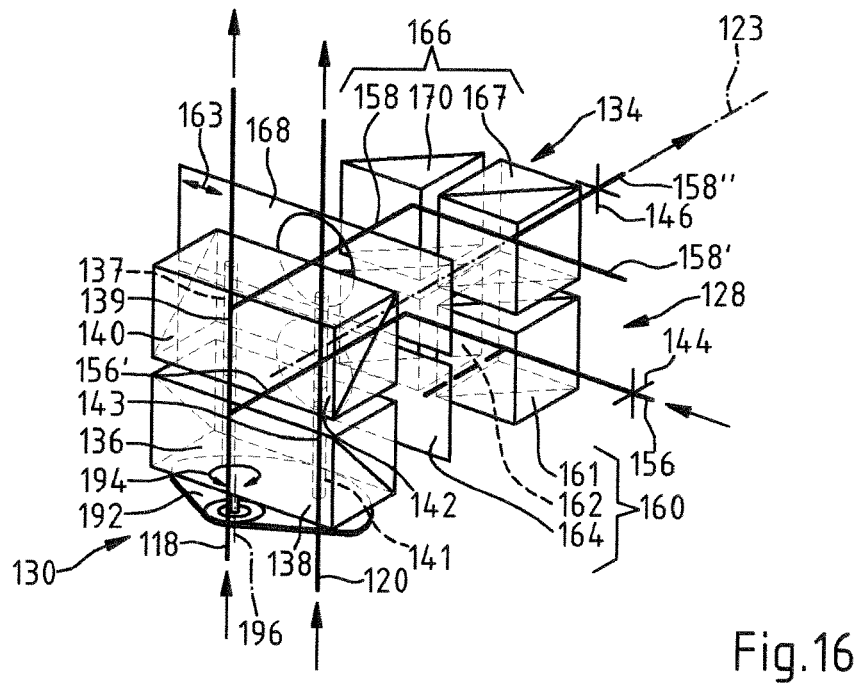
FIG. 16 and FIG. 17 show a further module assembly for use in an operating microscope with a shutter.
Figure 17:
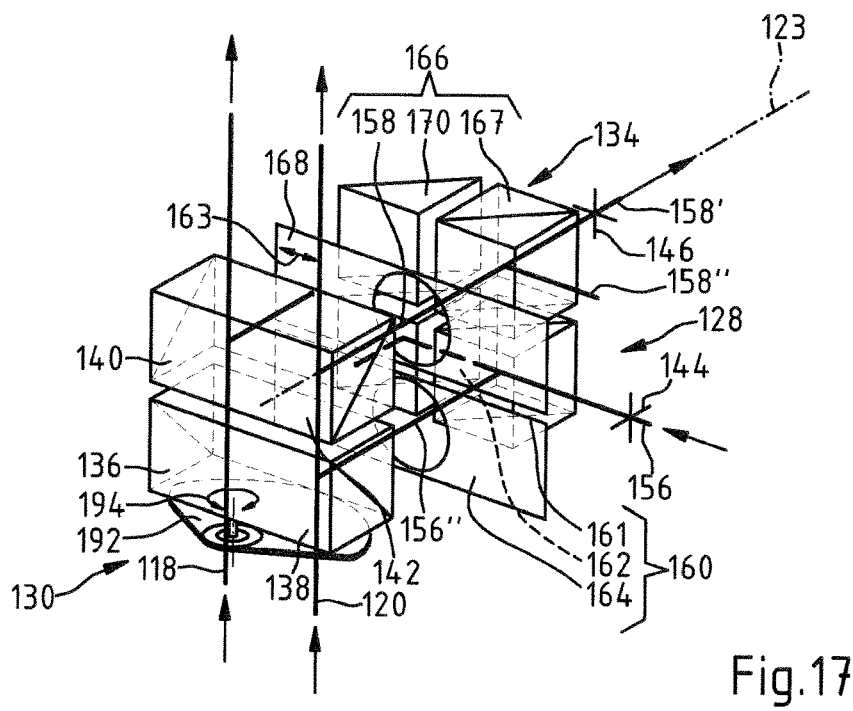

FIG. 16 and FIG. 17 show a further module assembly 130 for use in a stereoscopic operating microscope with stereoscopic partial beam paths (118, 120), a beam path 156 which has been guided to an optical interface 144 and which can be coupled into the first or the second stereoscopic partial beam path (118, 120) as a partial beam path (156', 156"), and with a beam path 158 which is provided at an optical interface 146 and which is decoupled from the first or second stereoscopic partial beam path (118, 120).

The module assembly 130 is an optics module and it contains an input coupling module 128. The input coupling module 128 has an adjustable optics assembly 160, which comprises a beam splitter 161 embodied as a splitter cube and which contains a mirror element 162 embodied as a deflection prism and a perforated diaphragm 164 arranged in a linearly movable manner as a further optical element embodied as a shutter element.

In the module assembly 130 there is an output coupling module 134 having an adjustable optics assembly 166 containing an optical element in the form of a beam splitter 167 and a further optical element, which is a shutter element in the form of a perforated diaphragm 168 arranged in a linearly movable manner, as well as a further deflection prism 170 acting as a mirror element.

On the side facing the main objective of the microscope in an operating microscope, the module assembly 130 has a shutter 192, which can be rotated about the axis 196 parallel to the optical axis (139, 143) of the observation channels (137, 141) in the direction of the double-headed arrow 194, as explained above on the basis of FIGS. 12 to 15. As a result of this, it is possible to selectively enable or block the observation channel with the first or second stereoscopic partial beam path (118, 120), which passes through the first and/or second beam splitter (136, 138, 140, 142).

FIG. 16 shows the module assembly 130 in a first setting, in which the beam path 156 provided at the optical interface 144 is coupled into the first stereoscopic partial beam path 118. Here, the beam path provided at the optical interface 146 is a beam path 158 decoupled from the first stereoscopic partial beam path.

FIG. 17 shows the module assembly 130 in a second setting, in which the beam path 156 provided at the optical interface 144 is coupled into the second stereoscopic partial beam path 120 and the beam path provided at the optical interface 146 is a beam path 158 decoupled from the second stereoscopic partial beam path 120.

A beam path 156 guided to the optical interface 144 is split into a first partial beam path 156' and a second partial beam path 156" within the module assembly 130 by means of the beam splitter 161. Here, the mirror element 162 directs the partial beam path 156' to the beam splitter 136 arranged in the first stereoscopic partial beam path 118. The partial beam path 156" is guided to the second beam splitter 138 arranged in the second stereoscopic partial beam path 120. The perforated diaphragm 164 can be displaced in the direction of the double-headed arrow 163. As a result of this, it is possible to couple the first partial beam path 156' into the first stereoscopic partial beam path 118 in a first setting, with the second partial beam path 156" of the beam path 156 being interrupted by means of the perforated diaphragm 164, or to couple the second partial beam path 156" into the second stereoscopic partial beam path 120 in a second setting, with the first partial beam path 156' then being interrupted by means of the perforated diaphragm 164.

In the first setting of the module assembly 130 shown in FIG. 16, the mirror element 170 in the adjustable optics assembly 166 of the output coupling module 134 directs the beam path 158 decoupled by means of the beam splitter 140 from the first stereoscopic partial beam path 118 to the beam splitter 167. The beam splitter 167 splits the beam path 158 into a first and a second partial beam path (158', 158"). In the setting of the module assembly 130 shown in FIG. 16, the light rays decoupled from the stereoscopic partial beam path 118 are mirrored into the optical interface 146 along the partial beam path 158".

In the second setting of the module assembly 130 shown in FIG. 17, the light rays decoupled from the second stereoscopic partial beam path 120 by means of the beam splitter 142 pass through the splitter surface in the beam splitter 167. The beam splitter 167 splits the beam path 158 into a partial beam path 158' which passes through the beam splitter 167 and a partial beam path 158' which is deflected by the beam splitter 167. In the setting of the module assembly 130 shown in FIG. 17, the light rays decoupled from the stereoscopic partial beam path 118 are guided to the optical interface 146 along the partial beam path 158'.

The mirror element 162 and the mirror element 170 of the module assembly 130 are held in a support frame (not depicted in any more detail) at an adjustment device allowing the adjustment, about two mutually orthogonal movement axes, of the optical axis of the beam path deflected by means of the mirror element (162, 170).

In an operating microscope, the module assembly 130 renders it possible for image data information provided at the optical interface 144, which was mirrored into the first or into the second stereoscopic partial beam path (118, 120), to be, for the benefit of an observer, selectively displayed in a manner superposed on the image of the object region or displayed without the image of the object region. Here, the image perceivable by the observer in the stereoscopic partial beam path is available for a camera at the optical interface 146.

FIG. 18, FIG. 19, FIG. 20 and FIG. 21 show a further module assembly 230 in different settings for use in a stereoscopic operating microscope with stereoscopic partial beam paths (218, 220), a beam path 256 which has been guided to an optical interface 244 and a beam path 258 decoupled from a stereoscopic partial beam path at an optical interface 246.

The module assembly 230 has an input coupling module 228 and an output coupling module 234 with a common beam splitter 236 and a common beam splitter 238, through which the first stereoscopic partial beam path 218 and the second stereoscopic partial beam path 220 pass in an operating microscope. The beam splitters (236, 238) have a double function. They serve for simultaneously coupling and decoupling a beam path into or from the stereoscopic partial beam paths (218, 220).

The input coupling module 228 has an adjustable optics assembly 260, which comprises a beam splitter 261 embodied as a splitter cube. The adjustable optics assembly 260 furthermore contains a mirror element 262 embodied as a deflection prism and a perforated diaphragm 264 as a further optical element. Here, the perforated diaphragm 264 acts as a shutter element. It is arranged in a linearly movable manner and can be moved in the direction of the double-headed arrow 263.

The output coupling module 234 has an adjustable optics assembly 266 with an optical element in the form of a beam splitter 267, with a further optical element in the form of a perforated diaphragm 268 arranged in a linearly movable manner and acting as a shutter element, and with a further deflection prism 270, which acts as a mirror element.

A beam path 256' guided to the optical interface 244 is split into a first partial beam path 256' and a second partial beam path 256" by means of the beam splitter 261. The mirror element 262 directs the partial beam path 256" to the beam splitter 238 arranged in the first stereoscopic partial beam path 220. The partial beam path 256' is guided to the second beam splitter 236 arranged in the second stereoscopic partial beam path 218. The perforated diaphragm 264 can be displaced in the direction of the double-headed arrow 263. As a result of this, it is possible selectively to couple the first partial beam path 256' into the first stereoscopic partial beam path 218, with the second partial beam path 256" of the beam path 256 being interrupted by means of the perforated diaphragm 264, or to couple the second partial beam path 256" into the second stereoscopic partial beam path 220, with the first partial beam path 256' then being interrupted by means of the perforated diaphragm 264.

Figure 18:
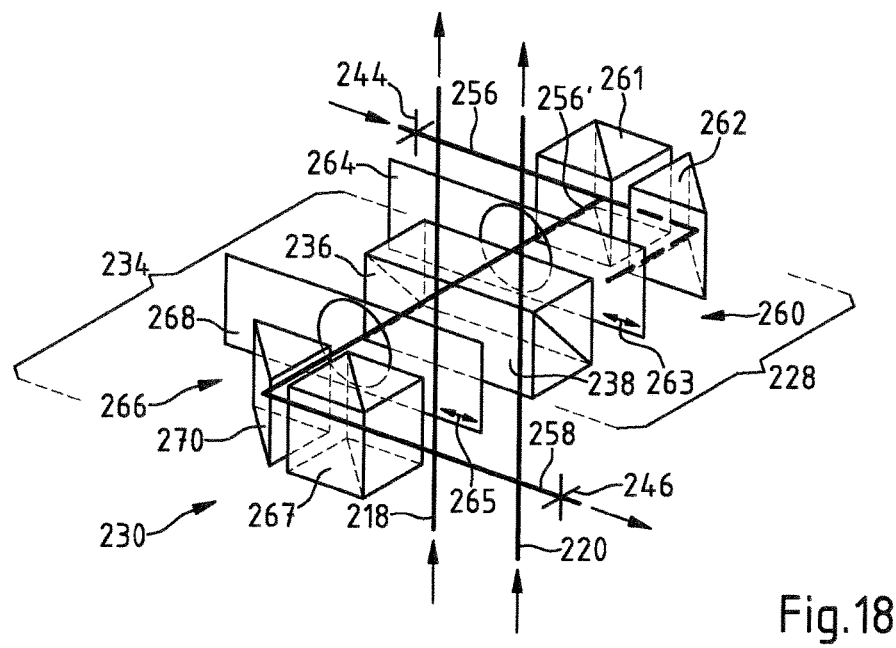
FIGS. 18 to 21 show a further module assembly for use in an operating microscope with a shutter.

In the setting of the module assembly 230 shown in FIG. 18, a beam path 256 provided at the optical interface 244 is coupled into the first stereoscopic partial beam path 218 as a beam path 256'. At the same time, a beam path 258 decoupled from the first stereoscopic partial beam path 218 is provided at the optical interface 246 in this case.

Figure 19:
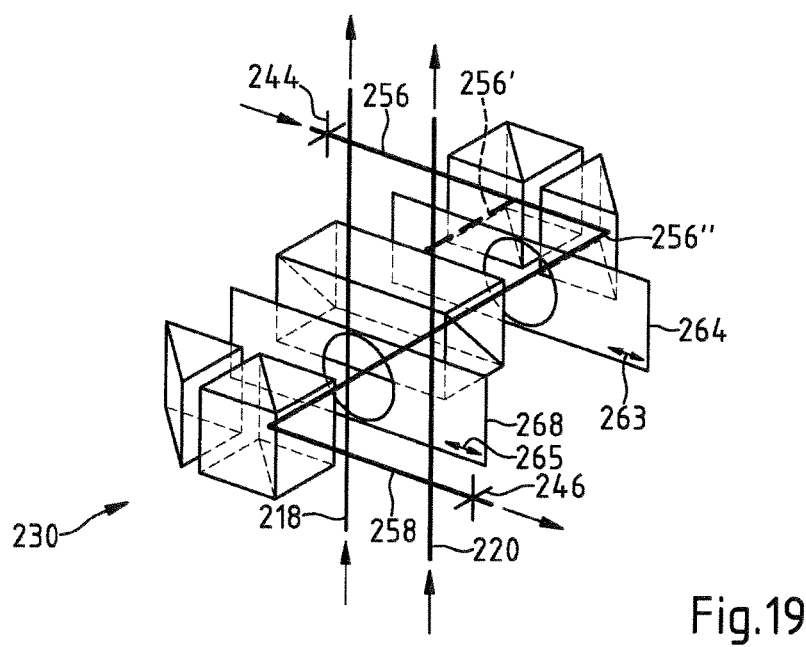

In FIG. 19, the module assembly 230 is shown in a second setting, with a beam path 256" coupled into the second stereoscopic partial beam path 220 and a beam path 258 decoupled from the stereoscopic partial beam path.

Figure 20:
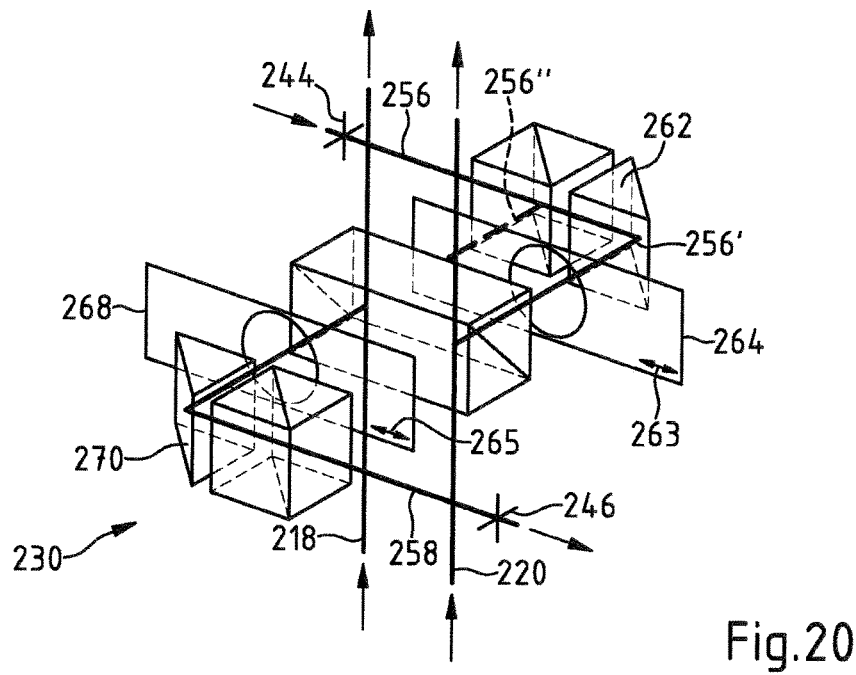

FIG. 20 shows the module assembly 230 in a third setting, with a beam path 256" coupled into the second stereoscopic partial beam path 220 and a beam path 258 decoupled from the first stereoscopic partial beam path 218.

Figure 21:
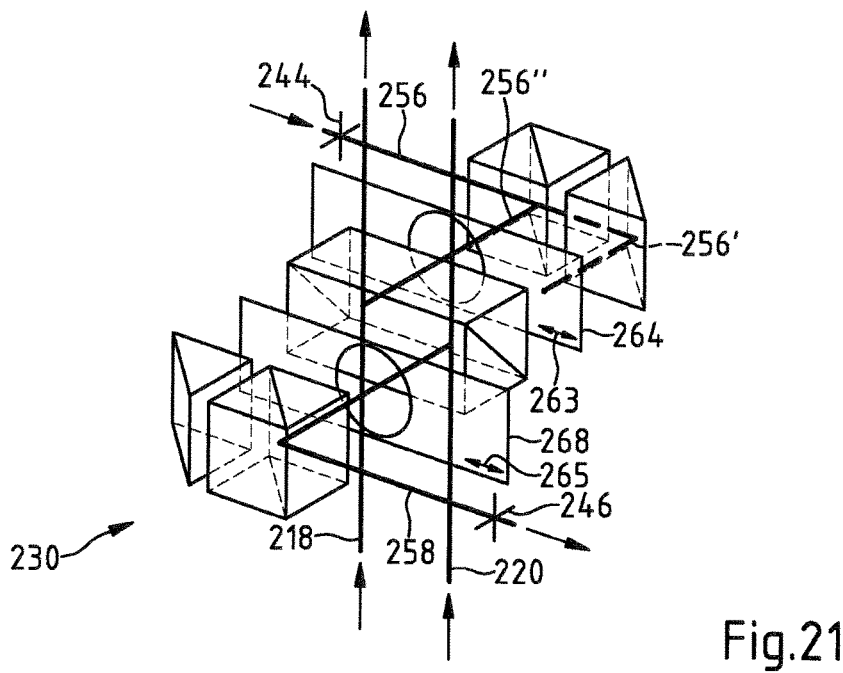

In FIG. 21, the module assembly 230 is shown in a fourth setting, with a beam path 256" coupled into the first stereoscopic partial beam path 218 and a beam path 258 decoupled from the second stereoscopic partial beam path 220.

The mirror element 262 and the mirror element 270 are held in a support frame (not depicted in any more detail) at an adjustment device allowing the adjustment, about two mutually orthogonal movement axes, of the optical axis of the beam path deflected by means of the mirror element (262, 270).

Compared to the module assemblies 30, 30' and 130 explained above, the module assembly 230 minimizes the light loss for the first and second stereoscopic partial beam path (218, 220) in an operating microscope because in this case each one of the stereoscopic partial beam paths (218, 220) only passes through one beam splitter and not two.

Moreover, the module assembly 230 has a reduced installation height in relation to the module assemblies 30, 30' and 130 and therefore enables particularly compact operating microscope configurations in the case of integration into operating microscopes. It should also be noted that the optical path lengths in the first and second stereoscopic partial beam paths (218, 220) are minimized in the module assembly 230.

In a modified embodiment of the module assembly 230, provision can be made for a shutter corresponding to the rotationally movable shutter 92 in the module assembly 30 in order thereby to selectively enable or block a stereoscopic partial beam path (218, 220) on the side facing the main objective of the microscope in an operating microscope. Hence, the module assembly 230 in an operating microscope enables the display of image information provided at the optical interface 244 in the first and second stereoscopic partial beam path (218, 220), selectively superposed on the image of an object region or without an image of the object region being visible.

FIGS. 22 to 27 show further input coupling modules for an operating microscope with different settings.

Figure 22:
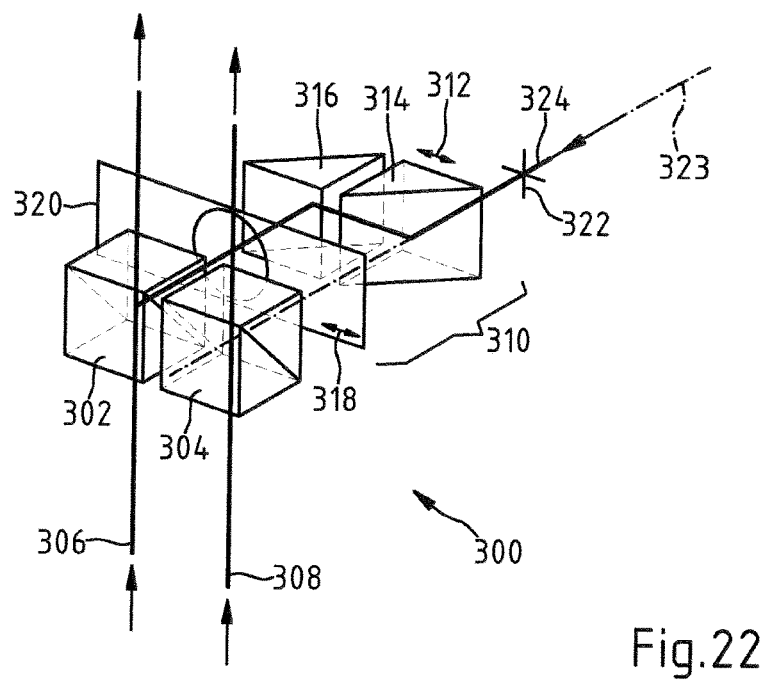
FIGS. 22 to 27 show various further input coupling modules for an operating microscope with different settings.

The input coupling module 300 shown in FIG. 22 has a first beam splitter 302 and has a second beam splitter 304, through which a first stereoscopic partial beam path 306 and a second stereoscopic partial beam path 308 pass in a stereoscopic operating microscope. The input coupling module 300 has an adjustable optics assembly 310 with a deflection prism 314 displaceable by linear movement in the direction of the double-headed arrow 312. The adjustable optics assembly 310 furthermore contains a deflection prism 316, which acts as a mirror element, and comprises a shutter element in the form of a perforated diaphragm 320 displaceable by linear movement in the direction of the double-headed arrow 318.

FIG. 22 shows the input coupling module 300 in a first setting. In the first setting of the input coupling module 300, shown in FIG. 22, a beam path 324 provided at the optical interface 322 is guided through the perforated diaphragm 320 to the first beam splitter 302 by way of the deflection prisms (314, 316) and therefore coupled into the first stereoscopic partial beam path 306.

Figure 23:
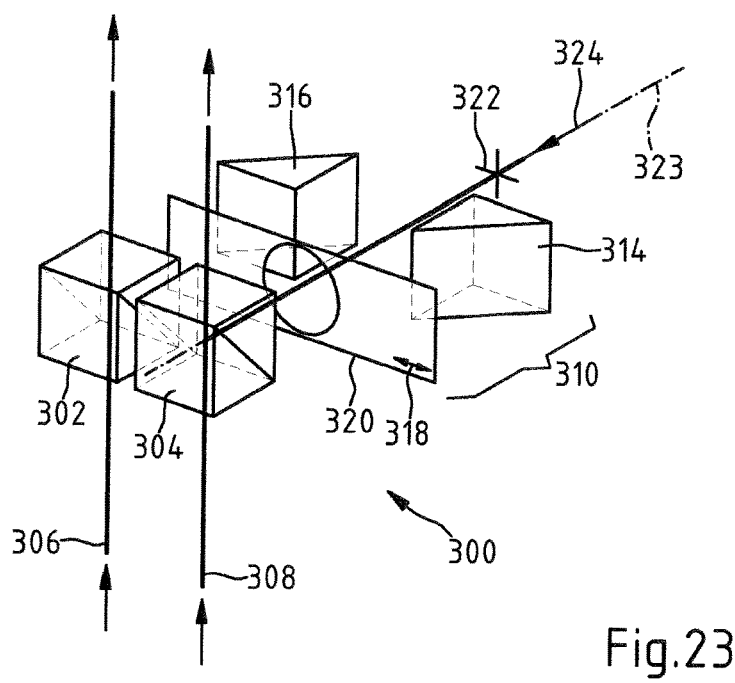

FIG. 23 shows the input coupling module 300 in a second setting that differs from the first setting. In the second setting of the input coupling module 300, the deflection prism 314 displaceable by linear movement is moved out of the beam path 324. The aperture of the perforated diaphragm 320 is situated in front of the second beam splitter 304 in this case, with the first beam splitter 302 being covered by means of the perforated diaphragm 320. The beam path 324 provided at the optical interface 322 in this case reaches through the aperture of the perforated diaphragm 320 and the second beam splitter 304 into the second stereoscopic partial beam path 308. Here, the optical interface 322 of the input coupling module 300 has an optical axis 323, which passes through the second beam splitter 304 and intersects the second stereoscopic partial beam path.

The input coupling module 400 shown in FIG. 24 once again has a first beam splitter 402 and has a second beam splitter 404, through which a first stereoscopic partial beam path 406 and a second stereoscopic partial beam path 408 pass in a stereoscopic operating microscope. The input coupling module 400 has an adjustable optics assembly 410 with a deflection prism 414 displaceable by linear movement in the direction of the double-headed arrow 412 and with a perforated diaphragm 420 which is movable in a linear manner in the direction of the double-headed arrow 418 and acts as a shutter element.

Figure 24:
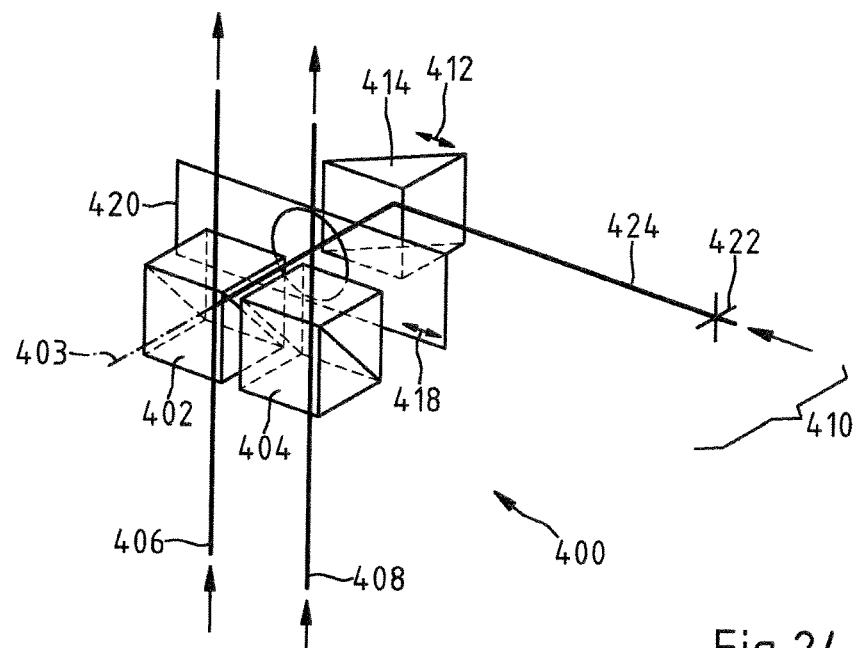

FIG. 24 shows the input coupling module 400 in a first setting. In the first setting of the input coupling module 400, shown in FIG. 24, a beam path 424 provided at the optical interface 422 is guided through the perforated diaphragm 420 in the direction of the optical axis 403 to the first beam splitter 402 by way of the deflection prism 414 and therefore coupled into the first stereoscopic partial beam path 406.

Figure 25:
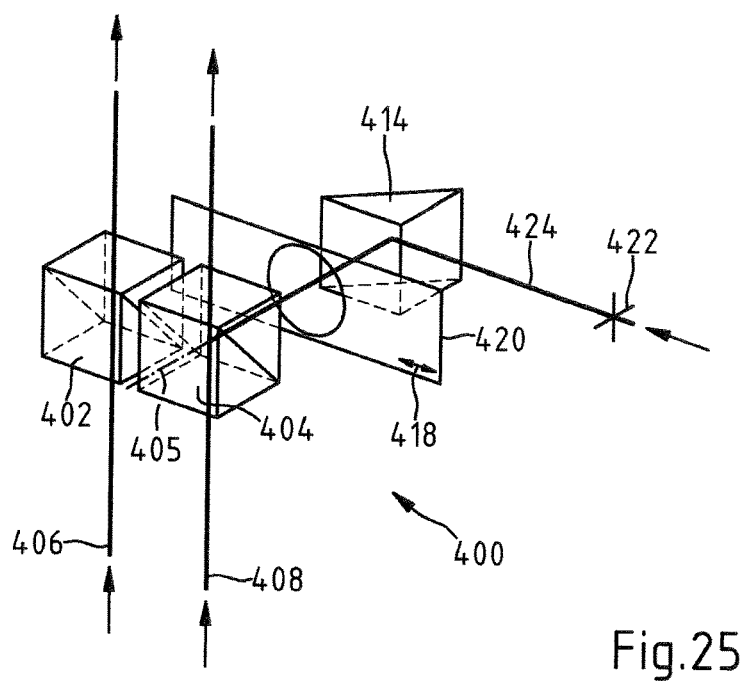

FIG. 25 shows the input coupling module 400 in a second setting that differs from the first setting. In the second setting of the input coupling module 400, the deflection prism 414 displaceable by linear movement is arranged upstream of the second beam splitter 404, together with the aperture of the perforated diaphragm 420. In this case, the aperture of the perforated diaphragm 420 is situated upstream of the second beam splitter 404. The beam path 424 provided at the optical interface 422 in this case reaches through the aperture of the perforated diaphragm 420 and the second beam splitter 404 along the direction of the optical axis 405 into the second stereoscopic partial beam path 408.

Figure 26:
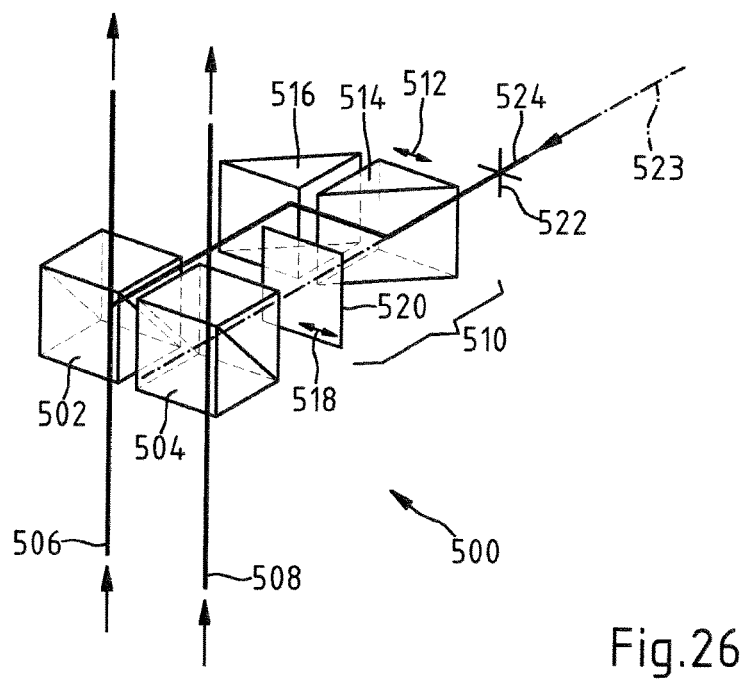

The input coupling module 500 shown in FIG. 26 also has a first beam splitter 502 and has a second beam splitter 504, through which a first stereoscopic partial beam path 506 and a second stereoscopic partial beam path 508 pass in a stereoscopic operating microscope. The input coupling module 500 has an adjustable optics assembly 510 with a first and a second deflection prism (514, 516) displaceable by linear movement in the direction of the double-headed arrow 512 and a shutter 520 displaceable by linear movement in the direction of the double-headed arrow 518.

FIG. 26 shows the input coupling module 500 in a first setting. In the first setting of the input coupling module 500, shown in FIG. 26, a beam path 524 provided at the optical interface 522 is guided to the first beam splitter 502 by way of the deflection prisms (514, 516) and therefore coupled into the first stereoscopic partial beam path 506.

Figure 27:
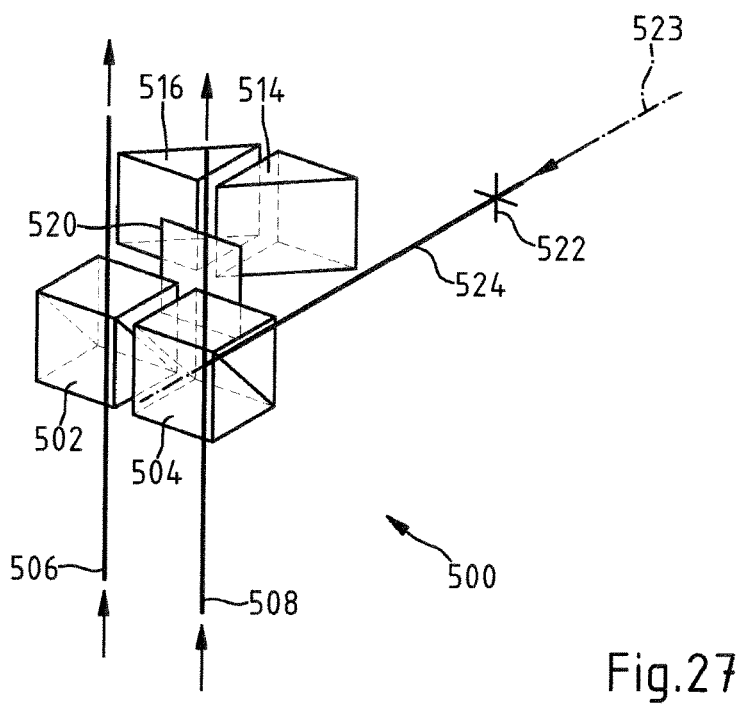

FIG. 27 shows the input coupling module 500 in a second setting that differs from the first setting. In the second setting of the input coupling module 500, the deflection prism 514 displaceable by linear movement and the deflection prism 516 coupled therewith are moved out of the beam path 524. In this case, the shutter 520 is situated upstream of the first beam splitter 502. The beam path 524 provided at the optical interface 522 in this case directly reaches the second beam splitter 504 and, from there, it reaches the second stereoscopic partial beam path 508.

It should be noted that, in a modified embodiment, a rhomboid prism with corresponding linear movability may be provided for the input coupling module 500 instead of the deflection prisms (514, 516) displaceable by linear movement.

The optical interface 522 of the input coupling module 500 has an optical axis 523, which passes through the beam splitter 504 and which intersects the stereoscopic partial beam path 508.

FIG. 28, FIG. 29, FIG. 30 and FIG. 31 show further output coupling modules for an operating microscope with different settings.

Figure 28:
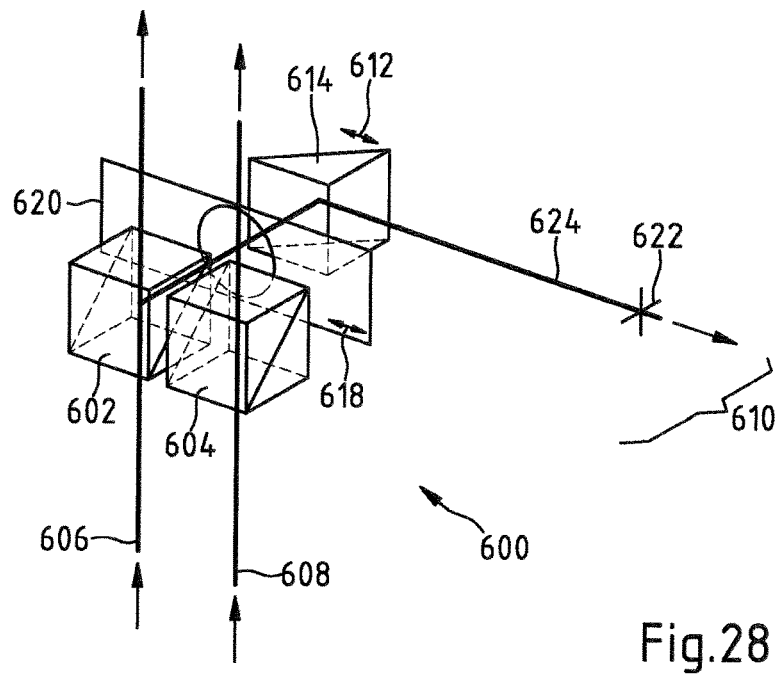
FIGS. 28 to 31 show various further output coupling modules for an operating microscope with different settings.
Figure 29:
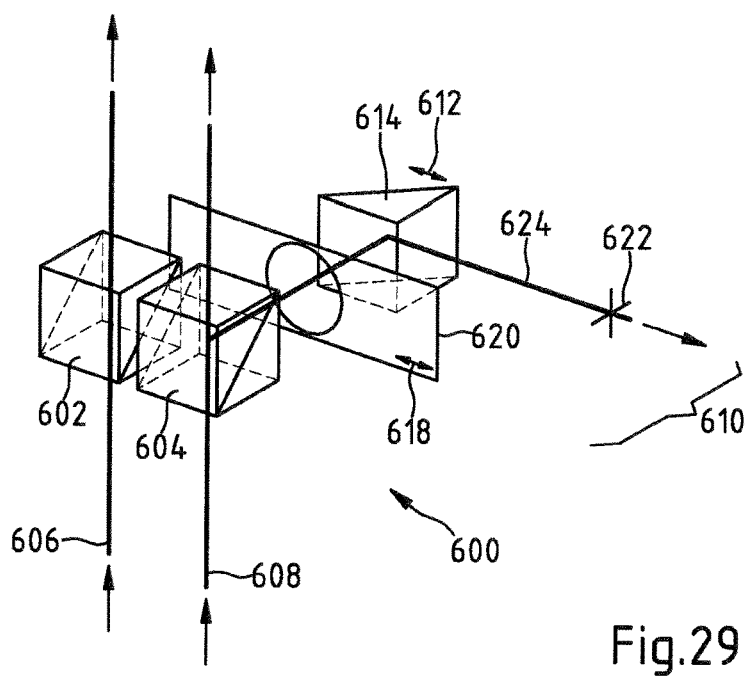

The output coupling module 600 shown in FIG. 28 and FIG. 29 corresponds to the input coupling module 300 explained on the basis of FIG. 24 and FIG. 25 in terms of configuration and function thereof. The output coupling module 700 shown in FIG. 30 and FIG. 31 corresponds to the input coupling module explained on the basis of FIG. 26 and FIG. 27 in terms of configuration of the function thereof.

Figure 30:
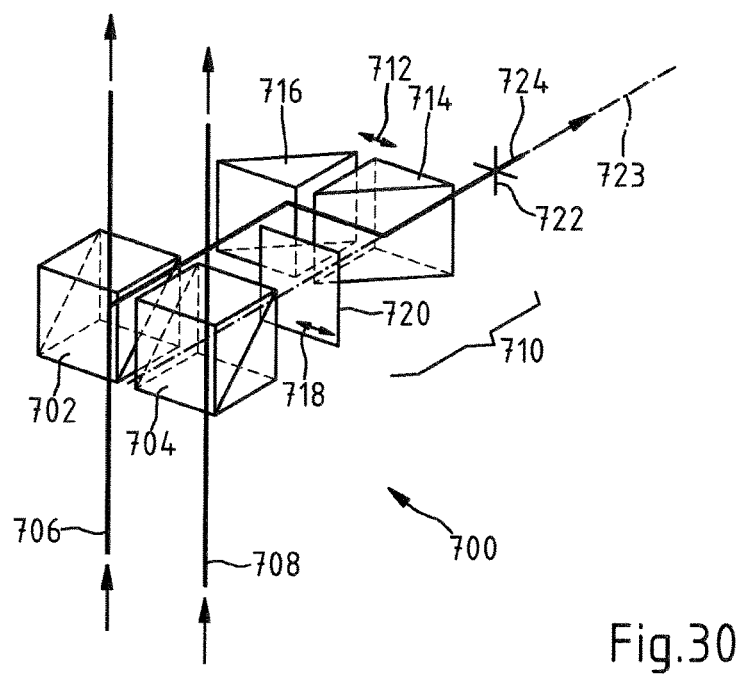
Figure 31:
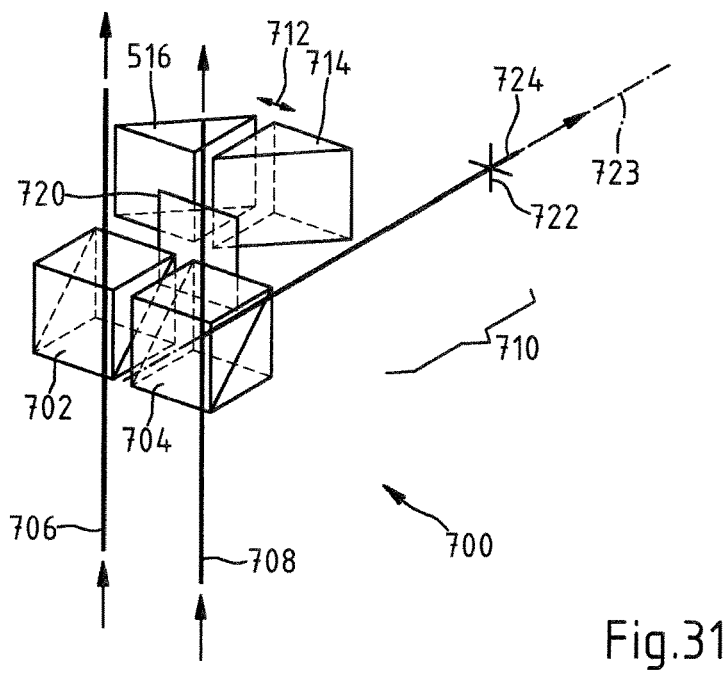

Assemblies and elements in FIG. 28 and FIG. 29 as well as in FIG. 30 and FIG. 31 which are identical to the assemblies and elements in FIG. 24 and FIG. 25 as well as in FIG. 26 and FIG. 27 have numbers as reference signs that, in FIG. 28 and FIG. 29, are increased by the number 200 in relation to FIGS. 24 and 25 and that, in FIG. 30 and FIG. 31, are increased by the number 200 in relation to FIG. 26 and FIG. 27. The beam path decoupled from the first or second stereoscopic partial beam path 606, 608 or 706, 708 has the reference sign (624, 724) in this case.

Further modifications and developments of input and output coupling modules according to the invention can also emerge by combining various features of the embodiments described above.

Figure 32:
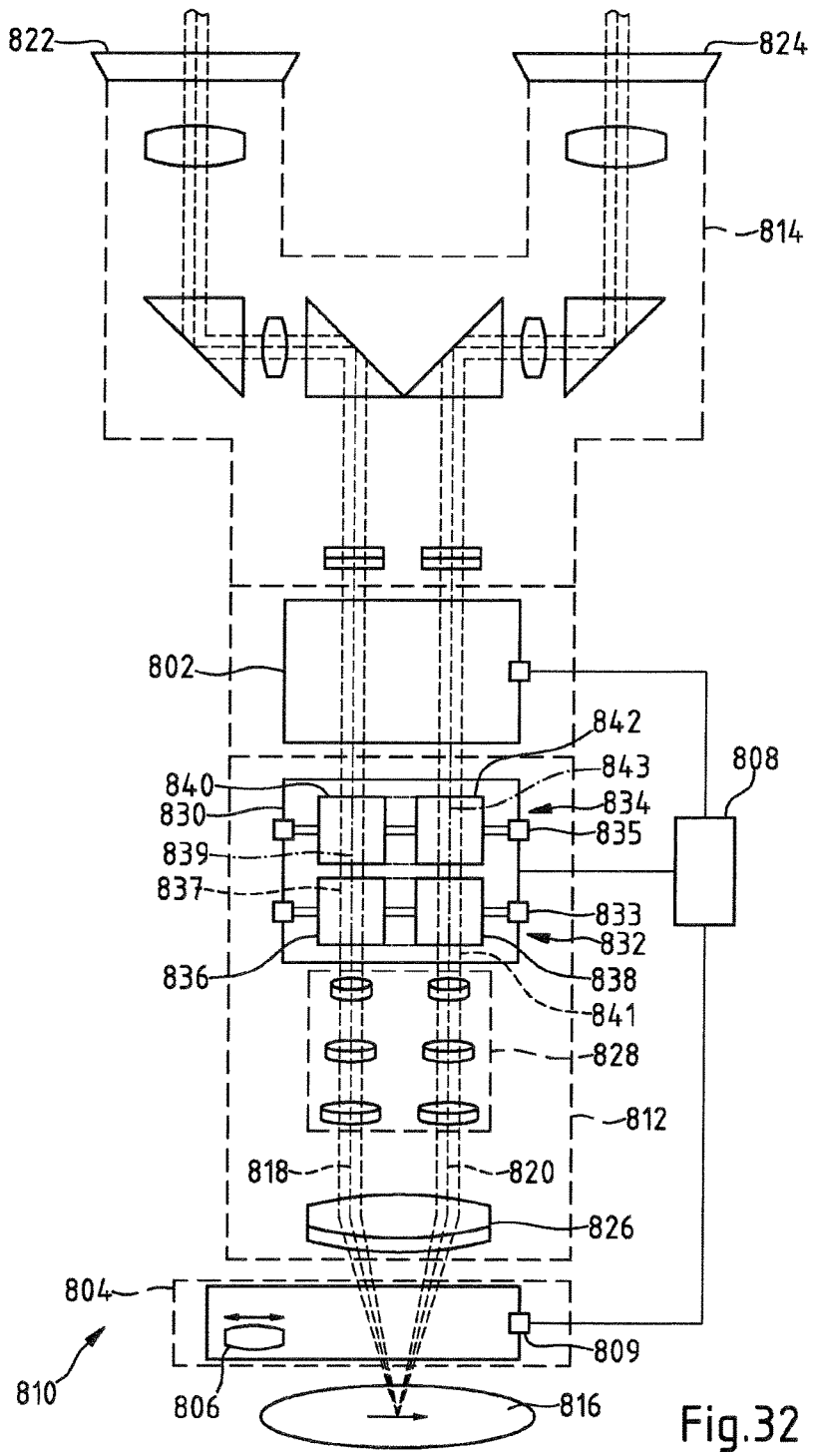
FIG. 32 shows a surgical microscope for stereoscopic observation of an object region, with a module assembly embodied as an input and output coupling module and with a system for interchanging the beam and image erection in a first setting; and, FIG. 33 shows the surgical microscope, shown in FIG. 32, with the system for interchanging the beam and image erection in a second setting.
Figure 33:
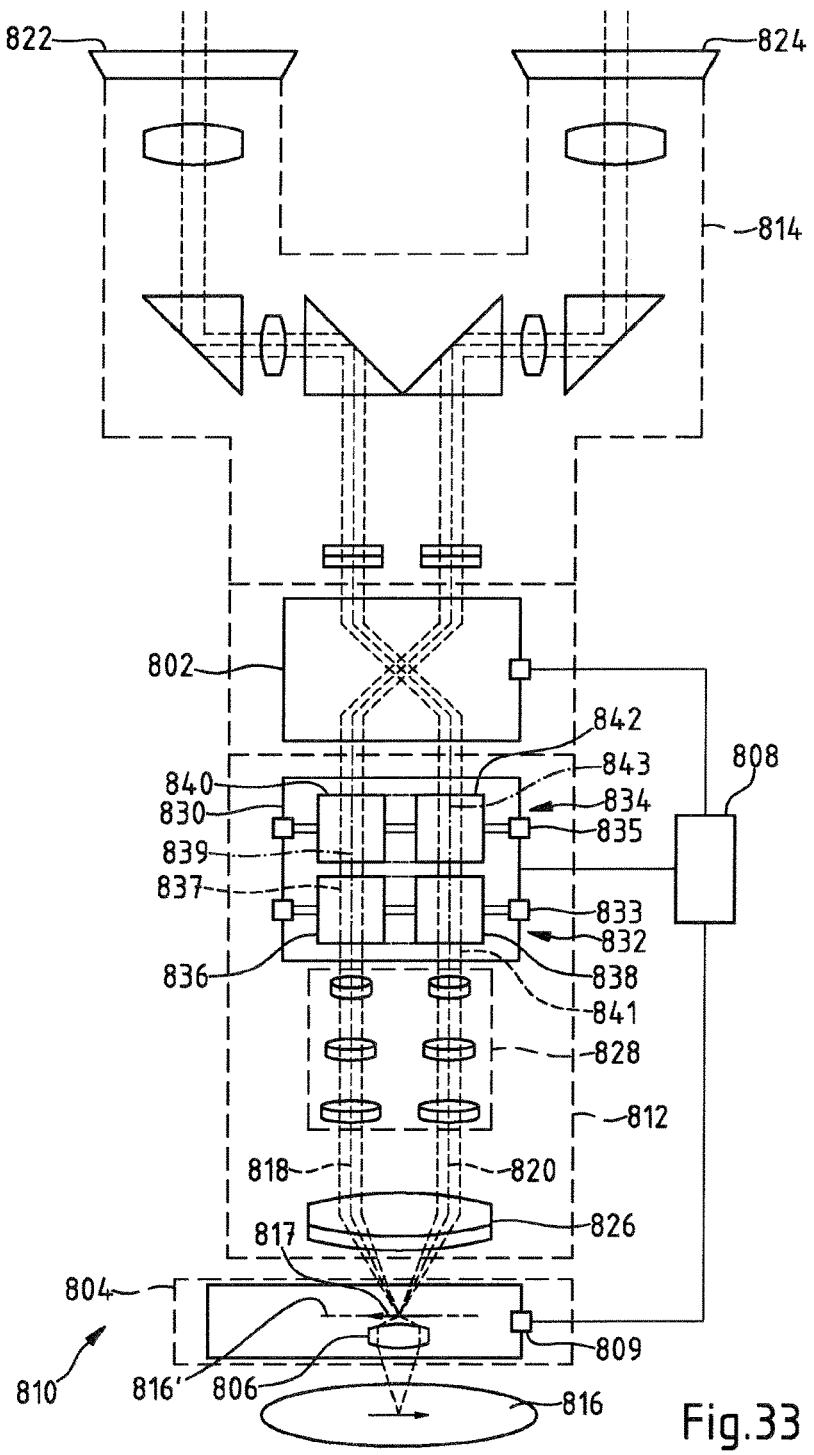

FIG. 32 shows an operating microscope 810 embodied as an ophthalmic operating microscope. To the extent that the assemblies in the operating microscope 810 functionally correspond to the assemblies in the operating microscope 10 described on the basis of FIG. 1, these have been identified in FIG. 32 by reference signs with a number that has been increased by the number 800 in relation to FIG. 1. The module assembly 830 contains an input coupling module 834 and an output coupling module 832, which preferably has a configuration as is described for both an input coupling module and an output coupling module on the basis of the figures above. The input coupling module 834 in the module assembly 830 serves for selective coupling of a beam path from a display into the first or the second stereoscopic partial beam path (818, 820). The output coupling module 832 in the module assembly 830 has the object of selectively decoupling a beam path to a camera from the first or the second stereoscopic partial beam path (818, 820). To this end, there respectively is in the input and output coupling module in the module assembly 830 a first and a second adjustable optics assembly for which at least two different settings are possible. The operating microscope 810 moreover contains a system for interchanging the beam and image erection 802 and comprises an ophthalmoscopy attachment module 804 with an ophthalmoscopy lens 806. In FIG. 32, the operating microscope 810 is shown with the ophthalmoscopy lens 806 moved out to the observation beam path. FIG. 33 shows the operating microscope 810 with an ophthalmoscopy lens 806 arranged in the observation beam path. In this case, the ophthalmoscopy lens 806 generates an inverted image 817 of the object region 816 in an intermediate image plane 816', which can be observed stereoscopically by an observer in the left and right eyepiece (822, 824) by way of the first and second stereoscopic partial beam path (818, 820).

There is a control device 808 in the operating microscope 810 for switching the module assembly 830 and the system for interchanging the beam and image erection 802. The control device acts as a coupling device, which couples the switching state of the system for interchanging the beam and image erection 802 with the setting, that is, the switching state of the input and output coupling module in the module assembly 830.

In this case, the control device 808 is also connected to the ophthalmoscopy attachment module 804. By means of a motor-driven drive 809 controlled by the control device 808, the ophthalmoscopy lens 806 can be selectively moved into the observation beam path and out of the observation beam path. When the ophthalmoscopy lens 806 is moved into the observation beam path, the control device 808 brings about a switching of the system for interchanging the beam and image reversal 802 and of the input and output coupling module (834, 832) in the module assembly 830. Here, the beam path from the display is coupled into a different stereoscopic partial beam path in relation to the setting prior to the switchover and a different stereoscopic partial beam path is guided to the camera in relation to the setting prior to the switchover.

In a modified embodiment of the operating microscope 810, a manual drive may also be provided instead of a motor-driven drive for moving the ophthalmoscopy lens 806 in the ophthalmoscopy attachment module 804. Here it is advantageous if the attachment module 804 contains a position sensor for registering the position of the ophthalmoscopy lens 806, the sensor being coupled to the control device 808 in order to bring about the switching over of the system for interchanging the beam and image erection 802 and of the input and output coupling module (834, 832) in the module assembly 830 when the ophthalmoscopy lens 806 is arranged.

It should be noted that the operating microscope 810, as a matter of principle, may be embodied with an ophthalmoscopy lens 806, even if it does not have an ophthalmoscopy attachment module 804. In order to observe the fundus of a patient eye, use must then simply be made of, for example, an indirect contact lens instead of the ophthalmoscopy lens 806.

In conclusion, the following should be registered. The invention relates to an input coupling module 128 for selectively coupling a beam path 156 into a first or second stereoscopic partial beam path (118, 120) in an operating microscope and with an optical interface 144 for guiding a beam path 156 to be coupled-in. The input coupling module 128 has a first beam splitter 136 arrangeable in the first stereoscopic partial beam path 118 and a second beam splitter 138 arrangeable in the second stereoscopic partial beam path 120. The input coupling module 128 contains an adjustable optics assembly 160, which selectively guides a beam path 156 provided at the optical interface 144 for coupling into the first or second stereoscopic partial beam path (118, 120) to the first beam splitter 136 or the second beam splitter 138. According to the invention, the adjustable optics assembly 160 comprises at least one optical element 164 displaceable by a linear movement from a first position to a second position, and vice versa, for switching the beam path, the displaceable optical element being arranged in the beam path 156 to be coupled-in in the first position and/or the second position. The invention moreover relates to an output coupling module 134 for selectively decoupling a beam path from a first or second stereoscopic partial beam path (118, 120) in an operating microscope, the output coupling module having an optical interface 146 for providing the beam path, a first beam splitter 140 arrangeable in the first partial beam path 118 and a second beam splitter 142 arrangeable in the second partial beam path. The output coupling module 134 moreover contains an adjustable optics assembly 166 which selectively guides a beam path 158 decoupled from the first or the second stereoscopic partial beam path to the optical interface 146. According to the invention, the adjustable optics assembly 166 comprises at least one optical element 168 displaceable by a linear movement from a first position to a second position, and vice versa, for switching the beam path 158, the displaceable optical element being arranged in the decoupled beam path 158 in the first position and/or the second position.

It is understood that the foregoing description is that of the preferred embodiments of the invention and that various changes and modifications may be made thereto without departing from the spirit and scope of the invention as defined in the appended claims.

LIST OF REFERENCE SIGNS

10 Surgical or operating microscope
12 Main body
14 Binocular tube
16 Object region
18, 20 Partial beam path
22 Left eyepiece
23 Optical axis
24 Right eyepiece
26 Main objective
28 Magnification system
30, 30' Module assembly
32 Output coupling module
33, 35 Support frame
34 Input coupling module
36, 38, 40, 42 Beam splitter
37, 41 Observation channels
39, 43, 45, 47 Optical axis
44, 46 Interfaces
50 Display module
54 Camera
56, 56', 56", 58 Beam path
60, 66 Optics assembly
61 Beam splitter
62 Mirror element
63 Double-headed arrow
64, 68 Perforated diaphragm
67, 70 Mirror element, deflection prism
72 Adjustment device
74 Holder
76 Fastening screw
78 Support
80, 82 Adjustment screws
83 Setscrew
84, 86 Movement axes
88, 90 Double-headed arrows
92 Shutter
94 Double-headed arrow
96 Parallel axis
118, 120 Partial beam path
123 Optical axis
128 Input coupling module
130 Module assembly
134 Output coupling module
136, 138, 140, 142 Beam splitter
137, 141 Observation channels
139, 143 Optical axes
144, 146 Optical interfaces
156, 156', 156" Partial beam path, beam path
158, 158', 158" Partial beam path, beam path
160, 166 Optics assembly
161, 167 Beam splitter
162 Mirror element
163 Double-headed arrow
164, 168 Perforated diaphragm
170 Mirror element, deflection prism
192 Shutter
194 Double-headed arrow
196 Parallel axis
218, 220 Partial beam path
228 Input coupling module
230 Module assembly
234 Output coupling module
236, 238 Beam splitter
244, 246 Interfaces
256, 256', 256", 258 Partial beam path, beam path
260 Optics assembly
261, 267 Beam splitter
262 Mirror element
263, 265 Double-headed arrow
264, 268 Perforated diaphragm
266 Optics assembly
270 Mirror element, deflection prism
300 Input coupling module
302, 304 Beam splitter
306, 308 Partial beam path
310 Optics assembly
312, 318 Double-headed arrow
314, 316 Mirror element, deflection prism
320 Perforated diaphragm
322 Optical interfaces
323 Optical axis
324 Beam path
400 Input coupling module
402, 404 Beam splitter
403, 405 Optical axis
406, 408 Partial beam path
410 Optics assembly
412 Double-headed arrow
414 Mirror element, deflection prism
418 Double-headed arrow
420 Perforated diaphragm
422 Optical interfaces
424 Beam path
500 Input coupling module
502, 504 Beam splitter
506, 508 Partial beam path
510 Optics assembly
512, 518 Double-headed arrow
514, 516 Mirror element, deflection prism
520 Shutter
522 Optical interfaces
523 Optical axis
524 Beam path
600 Output coupling module
602, 604 Beam splitter
606, 608 Partial beam path
610 Optics assembly
614 Mirror element, deflection prism
612, 618 Double-headed arrow
620 Perforated diaphragm
622 Interfaces
624 Beam path
700 Output coupling module
702, 704 Beam splitter
706, 708 Partial beam path
710 Optics assembly
712, 718 Double-headed arrow
714, 716 Mirror element, deflection prism
720 Shutter
722 Optical interfaces
723 Optical axis
724 Beam path
802 System for interchanging the beam and image erection
804 Ophthalmoscopy attachment module
806 Ophthalmoscopy lens
808 Control device
809 Drive
810 Operating microscope
812 Main body
814 Binocular tube
816 Object region
816' Intermediate image plane 817 Image
818, 820 Partial beam path
822 Left eyepiece
824 Right eyepiece
826 Main objective
828 Zoom system, Magnification system
830 Module assembly
832 Output coupling module
833, 835 Support frame
834 Input coupling module
836, 838, 840, 842 Beam splitter
837, 841 Observation channels
839, 843 Optical axes

What is claimed is:

1. In an optical instrument defining first and second stereoscopic component beam paths, an optical unit defining a beam path, an incoupling module for selectively coupling said beam path from said optical unit into said first stereoscopic component beam path or into said second stereoscopic component beam path, said optical unit and said incoupling module conjointly defining an optical interface through which said beam path passes from said optical unit to said incoupling module, said incoupling module comprising:
   a first beam splitter arranged in said first stereoscopic component beam path;
   a second beam splitter arranged in said second stereoscopic component beam path;
   an adjustable optics assembly configured to selectively direct the beam path to the first beam splitter or the second beam splitter;
   the adjustable optics assembly including a first mirror element displaceable by linear movement from a first position to a second position and vice versa relative to the optical interface;
   said first mirror element being disposed in the beam path in the first position thereof;
   the adjustable optics assembly further including a second mirror element spatially fixed with respect to said optical interface and configured to direct said beam path to said first beam splitter for coupling said beam path into said first stereoscopic component beam;
   said first mirror element, in said first position, being configured to direct the beam path to said second mirror element for coupling into said first beam splitter, and, in said second position, clearing said beam path to the second beam splitter for coupling said beam path directly into the second stereoscopic component beam without deflection of said incoupling beam path between said interface and said second beam splitter; and,
   said beam path defining an optical axis which is an axis of symmetry passing through said second beam splitter when said first mirror element is in said second position.

2. In an optical instrument defining first and second stereoscopic component beam paths, an optical unit and an outcoupling module conjointly defining an optical interface, the outcoupling module being configured for selectively decoupling a beam path from said first stereoscopic component beam path or from said second stereoscopic component beam path toward the optical interface so as to pass therethrough to the optical unit, said outcoupling module comprising:
   a first beam splitter arranged in said first stereoscopic component beam path;
   a second beam splitter arranged in said second stereoscopic component beam path;
   an adjustable optics assembly configured to guide the decoupled beam path to said optical interface selectively from said first beam splitter or said second beam splitter;
   said adjustable optics assembly including a first mirror element displaceable by linear movement from a first position to a second position and vice versa relative to said optical interface;
   said first mirror element being arranged in the beam path guided to said optical interface in said first position;
   said adjustable optics assembly further including a second mirror element which is spatially fixed with respect to said optical interface and to which said beam path is directed from said second beam splitter for outcoupling out of said second stereoscopic component beam path;
   said first mirror element, in the first position, receiving said beam path guided from said second mirror element and deflecting the decoupled beam path from the second stereoscopic component beam path directly to said optical interface, and, in the second position, clearing a beam path from said first beam splitter directly to said optical interface for outcoupling out of said first stereoscopic component beam path to the optical interface without deflection of the outcoupling beam path between said first beam splitter and said optical interface; and,
   at the optical interface, the optical axis of the beam path is an axis of symmetry passing through the first beam splitter.

3. In an optical instrument defining first and second stereoscopic component beam paths, an optical unit defining a beam path, an incoupling module for selectively coupling said beam path into said first stereoscopic component beam path or into said second stereoscopic component beam path, said incoupling module and said optical unit conjointly defining an optical interface through which said beam path passes from said optical unit to said incoupling module, said incoupling module comprising:
   a first beam splitter arranged in said first stereoscopic component beam path;
   a second beam splitter arranged in said second stereoscopic component beam path;
   an adjustable optics assembly configured to selectively direct the beam path to the first beam splitter or the second beam splitter;
   the adjustable optics assembly including a single mirror element displaceable by linear movement from a first position to a second position and vice versa relative to the optical interface;
   said single mirror element being arranged in the beam path in the first position thereof and guiding said beam path to said first beam splitter for coupling into said first stereoscopic component beam path;
   said single mirror element being arranged in said beam path in the second position to guide the beam path to the second beam splitter for coupling into the second stereoscopic component beam path; and,
   the adjustable optical assembly containing a shutter element displaceable by linear movement and coupled as to movement with the single mirror element displaceable by linear movement, for selectively covering the first beam splitter and uncovering the second beam splitter or uncovering the first beam splitter and covering the second beam splitter.

4. In an optical instrument defining first and second stereoscopic component beam paths, an optical unit and an outcoupling module conjointly defining an optical interface, the outcoupling module being configured for selectively decoupling a beam path from said first stereoscopic component beam path or from said second stereoscopic component beam path toward the optical interface so as to pass therethrough to the optical unit, said outcoupling module comprising:
- a first beam splitter arranged in said first stereoscopic component beam path;
- a second beam splitter arranged in said second stereoscopic component beam path;
- an adjustable optics assembly which selectively guides the beam path decoupled from the first or the second stereoscopic component beam path to said optical interface;
- said adjustable optics assembly includes a single mirror element, which is displaceable by linear movement from a first position to a second position and vice versa relative to said optical interface;
- said single mirror element being arranged in the decoupled beam path in the first position and receiving the beam path from the first beam splitter for decoupling from the first stereoscopic component beam path;
- said single mirror element being arranged in said beam path to be decoupled also in the second position and said mirror element receiving the beam path from said second beam splitter for decoupling from said second stereoscopic component beam path; and,
- the adjustable optical assembly containing a shutter element displaceable by linear movement and coupled as to movement with the single mirror element displaceable by linear movement, for selectively covering the first beam splitter and uncovering the second beam splitter or uncovering the first beam splitter and covering the second beam splitter.

5. The incoupling module of claim 1, wherein said incoupling module further comprises a support frame receiving the optics assembly, in which support frame the second mirror element is held at an adjustment device wherein the second mirror element can be adjusted for setting the optical axis of the beam path guided to the first beam splitter.

6. The incoupling module of claim 1, wherein said incoupling module further comprises a support frame receiving the optics assembly, in which support frame the mirror element is held at an adjustment device wherein the mirror is adjusted for setting the optical axis of the beam path guided to the first beam splitter and the second beam splitter.

7. In an optical instrument defining first and second stereoscopic component beam paths, an optical unit defining a beam path, an incoupling module for selectively coupling said beam path into said first stereoscopic component beam path or into said second stereoscopic component beam path, said incoupling module and said optical unit conjointly defining an optical interface across which said beam path passes from said optical unit to said incoupling module, said incoupling module comprising:
- a first beam splitter arranged in said first stereoscopic component beam path;
- a second beam splitter arranged in said second stereoscopic component beam path;
- an adjustable optics assembly configured to selectively direct the beam path to the first beam splitter or the second beam splitter;
- said adjustable optics assembly including a shutter element for selectively covering the first beam splitter and uncovering the second beam splitter and vice versa;
- said shutter element being displaceable by linear movement from a first position to a second position and vice versa relative to the optical interface;
- said adjustable optics assembly further including a third beam splitter, which is stationary and splits the beam path, which is guided to the optical interface and coupled-in, into a first component beam path and into a second component beam path, wherein the first component beam path is guided to the second beam splitter and the second component beam path is guided to a stationary mirror element which deflects the second component beam path to the first beam splitter; and,
- said shutter element interrupting said first component beam when in said first position thereof and allowing said second component beam to pass to said first beam splitter and in said second position, interrupting said second component beam and allowing said first component beam to pass to said second beam splitter.

8. In an optical instrument defining first and second stereoscopic component beam paths, an optical unit and an outcoupling module conjointly defining an optical interface, the outcoupling module being configured for selectively decoupling a beam path from said first stereoscopic component beam path or said second stereoscopic component beam path toward the optical interface so as to pass therethrough to the optical unit, said outcoupling module comprising:
- a first beam splitter arranged in said first stereoscopic component beam path;
- a second beam splitter arranged in said second stereoscopic component beam path;
- an adjustable optics assembly configured to selectively guide the beam path to said optical interface from the first beam splitter or the second beam splitter;
- said adjustable optics assembly including only one movable element in the form of a shutter element for selectively covering said first beam splitter and uncovering said second beam splitter and vice versa;
- said shutter element being displaceable relative to said optical interface by linear movement from a first position wherein said first beam splitter is enabled and said second beam splitter is covered to a second position wherein said second beam splitter is enabled and said first beam splitter is covered;
- said adjustable optics assembly including a third beam splitter which is stationary and splits the beam path guided to the optical interface into a first component beam path and into a second component beam path;
- said first beam splitter decoupling the beam path from the first stereoscopic component beam path to a stationary mirror element;
- said stationary mirror element deflecting the beam path to the third beam splitter which directs the beam path as a component beam path to said optical interface; and,
- said second beam splitter directing the beam path from the second stereoscopic component beam path to the third beam splitter which enables the beam path to pass as a component beam path to said optical interface.

9. The outcoupling module of claim 8, wherein the optical axis of the beam path provided at said interface is an axis of symmetry passing through said third beam splitter.

10. The outcoupling module of claim 8, wherein the optical axis of the beam path provided at said interface passes through said second beam splitter.

11. The outcoupling module of claim 8, wherein a support frame receives the adjustable optics assembly, in which support frame the mirror element is held at an adjustment device configured to adjust the mirror element for setting the optical axis of the beam path guided to said first beam splitter.

12. An optical instrument comprising:
optics defining first and second stereoscopic component beam paths;
an optical unit defining a beam path;
an incoupling module for selectively coupling said beam path from said optical unit into said first stereoscopic component beam path or into said second stereoscopic component beam path;
said optical unit and said incoupling module conjointly defining an optical interface through which said beam path passes from said optical unit to said incoupling module;
said incoupling module comprising:
a first beam splitter arranged in said first stereoscopic component beam path;
a second beam splitter arranged in said second stereoscopic component beam path;
an adjustable optics assembly configured to selectively direct the beam path to the first beam splitter or the second beam splitter;
the adjustable optics assembly including a first mirror element displaceable by linear movement from a first position to a second position and vice versa relative to the optical interface;
said first mirror element being disposed in the beam path in the first position thereof;
the adjustable optics assembly further including a second mirror element configured to direct said beam path to said first beam splitter for coupling said beam path into said first stereoscopic component beam path;
said first mirror element, in said first position, being configured to direct the beam path to said second mirror element for coupling into said first beam splitter, and, in said second position, clearing said beam path to the second beam splitter for coupling said beam path directly into the second stereoscopic component beam path without deflection of said incoupling beam path between said interface and said second beam splitter; and,
said beam path defining an optical axis which is an axis of symmetry passing through said second beam splitter when said first mirror element is in said second position.

13. The incoupling module of claim 1, wherein said first mirror element is the only movable mirror element in said incoupling module and said second mirror element is stationary.

14. The outcoupling module of claim 2, wherein said first mirror element is the only movable mirror element in said incoupling module and said second mirror element is stationary.

15. The incoupling module of claim 3, wherein said mirror element is the only linearly movable mirror element of said incoupling module.

16. The outcoupling module of claim 4, wherein said mirror element is the only movable mirror element of said outcoupling module.

17. The optical instrument of claim 12, wherein said first mirror element is the only movable mirror element of said incoupling module and said second mirror element is stationary.

* * * * *